US010010606B2

(12) United States Patent
Korber et al.

(10) Patent No.: US 10,010,606 B2
(45) Date of Patent: Jul. 3, 2018

(54) MOSAIC CONSERVED REGION HIV IMMUNOGENIC POLYPEPTIDES

(71) Applicants: Los Alamos National Security, LLC, Los Alamos, NM (US); Isis Innovation Limited, Oxford (GB)

(72) Inventors: Bette T. M. Korber, Los Alamos, NM (US); Tomas Hanke, Oxford (GB); Andrew McMichael, Oxford (GB)

(73) Assignees: Los Alamos National Security, LLC, Los Alamos, NM (US); Oxford University Innovation Limited, Oxford (GB)

(*) Notice: Subject to any disclaimer, the term of this patent is extended or adjusted under 35 U.S.C. 154(b) by 0 days.

(21) Appl. No.: 15/025,733

(22) PCT Filed: Sep. 30, 2014

(86) PCT No.: PCT/US2014/058422
§ 371 (c)(1),
(2) Date: Mar. 29, 2016

(87) PCT Pub. No.: WO2015/048785
PCT Pub. Date: Apr. 2, 2015

(65) Prior Publication Data
US 2016/0213772 A1 Jul. 28, 2016

Related U.S. Application Data

(60) Provisional application No. 61/884,705, filed on Sep. 30, 2013.

(51) Int. Cl.
*A61K 39/21* (2006.01)
*A61K 39/12* (2006.01)
*C07K 14/005* (2006.01)

(52) U.S. Cl.
CPC .............. *A61K 39/21* (2013.01); *A61K 39/12* (2013.01); *C07K 14/005* (2013.01); *C12N 2740/16034* (2013.01)

(58) Field of Classification Search
None
See application file for complete search history.

(56) References Cited

U.S. PATENT DOCUMENTS

2005/0137387 A1  6/2005  Mullins et al.
2010/0266635 A1  10/2010 Hanke et al.
(Continued)

FOREIGN PATENT DOCUMENTS

WO   WO 2010/040847   4/2010
WO   WO 2015/048796   4/2015
WO   WO 2015/148602   10/2015

OTHER PUBLICATIONS van Harmelen et al. AIDS Res. Human Retrovir. 2001; 17(16): 1527-1531.*
(Continued)

*Primary Examiner* — Janet L Andres
*Assistant Examiner* — Stuart W Snyder
(74) *Attorney, Agent, or Firm* — Klarquist Sparkman, LLP

(57) ABSTRACT

Disclosed herein are mosaic conserved region HIV polypeptides and immunogenic polypeptides including one or more of the mosaic conserved region polypeptides. In some embodiments, the immunogenic polypeptides are included in an immunogenic composition, such as a polyvalent immunogenic composition. Also disclosed herein are methods for treating or inhibiting HIV in a subject including administering one or more of the disclosed immunogenic polypeptides or compositions to a subject having or at risk of HIV infection. In some embodiments, the methods include inducing an immune response in a subject compris-
(Continued)

Figure 1A:
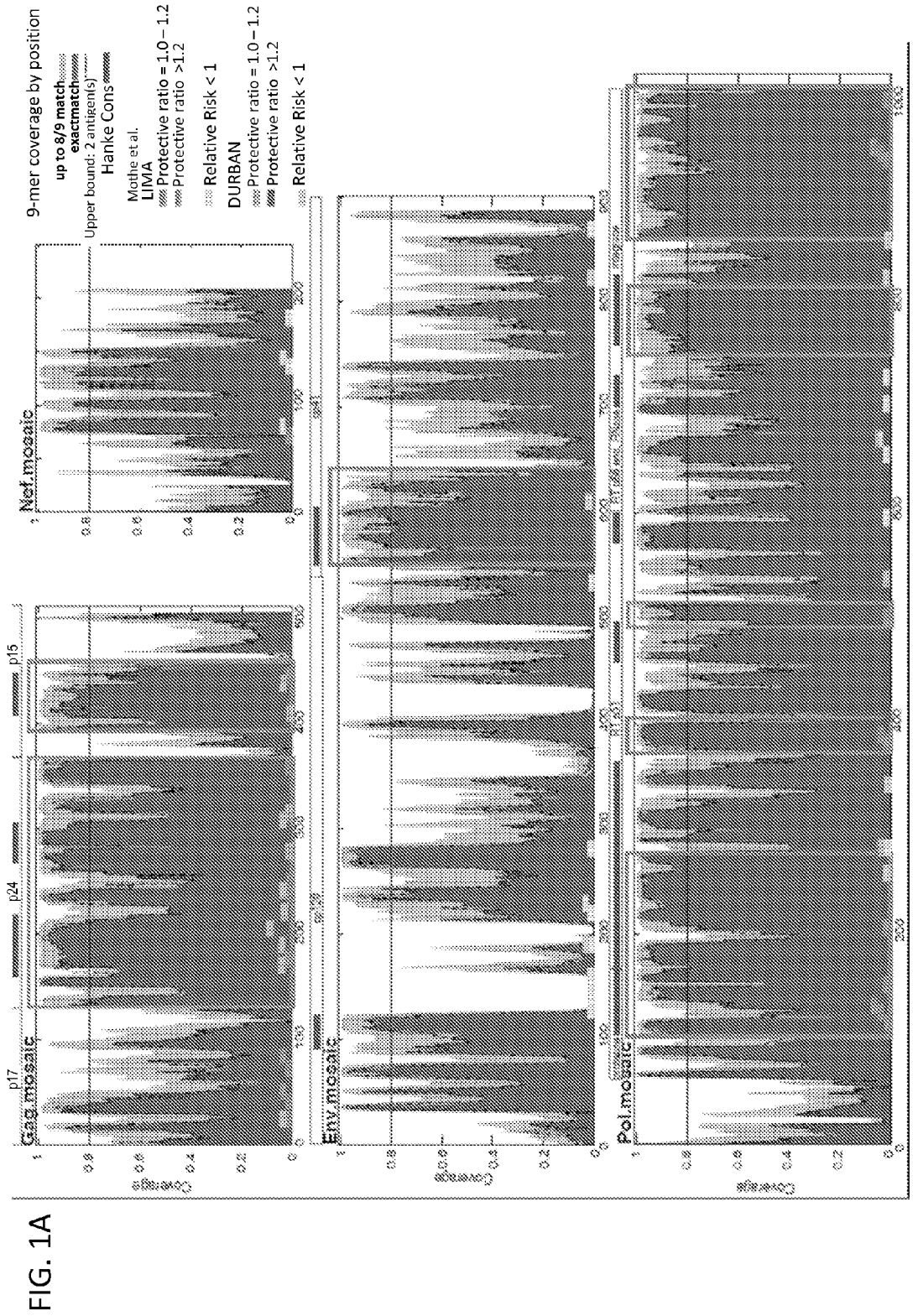
Figure 1B:
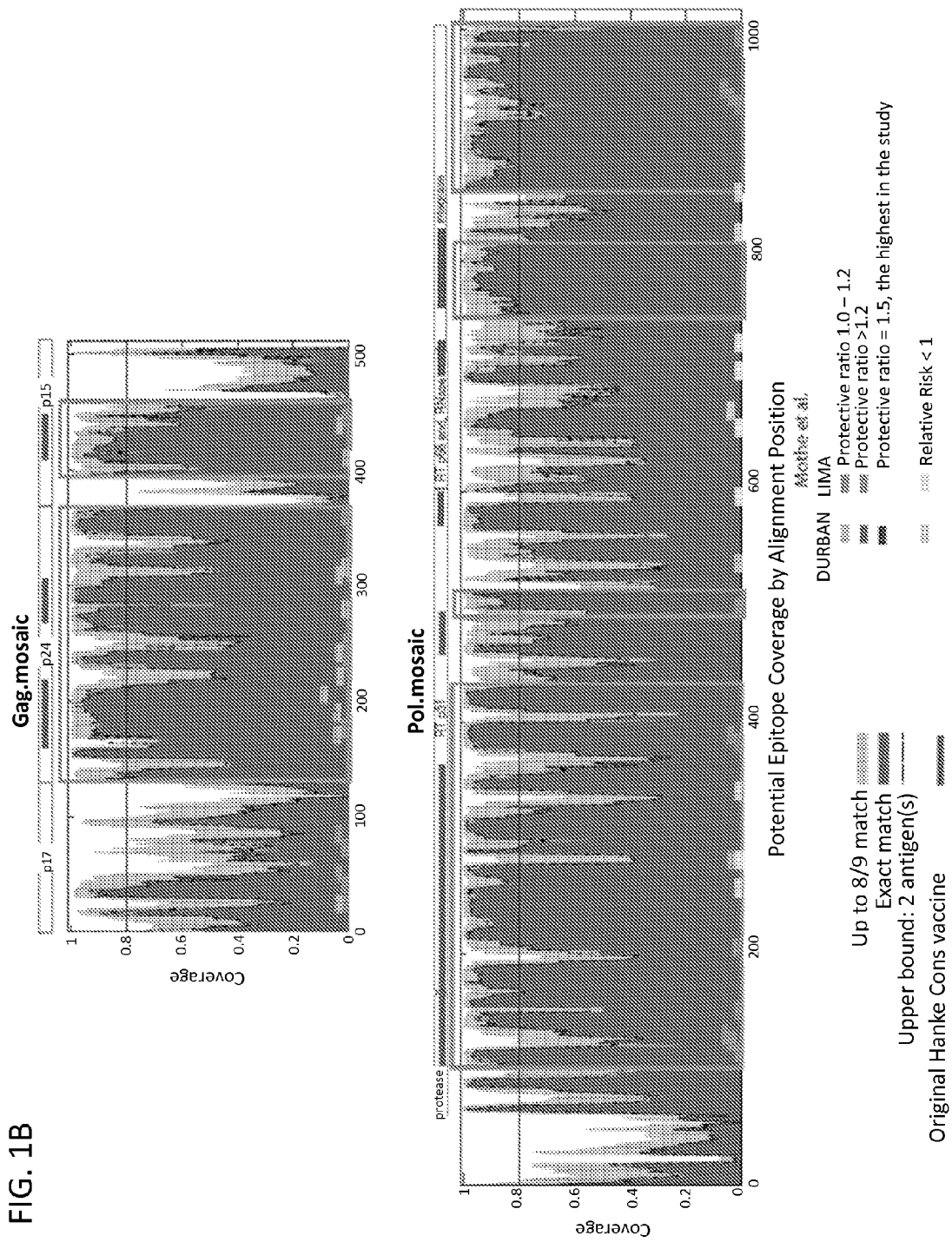
Figure 2A:
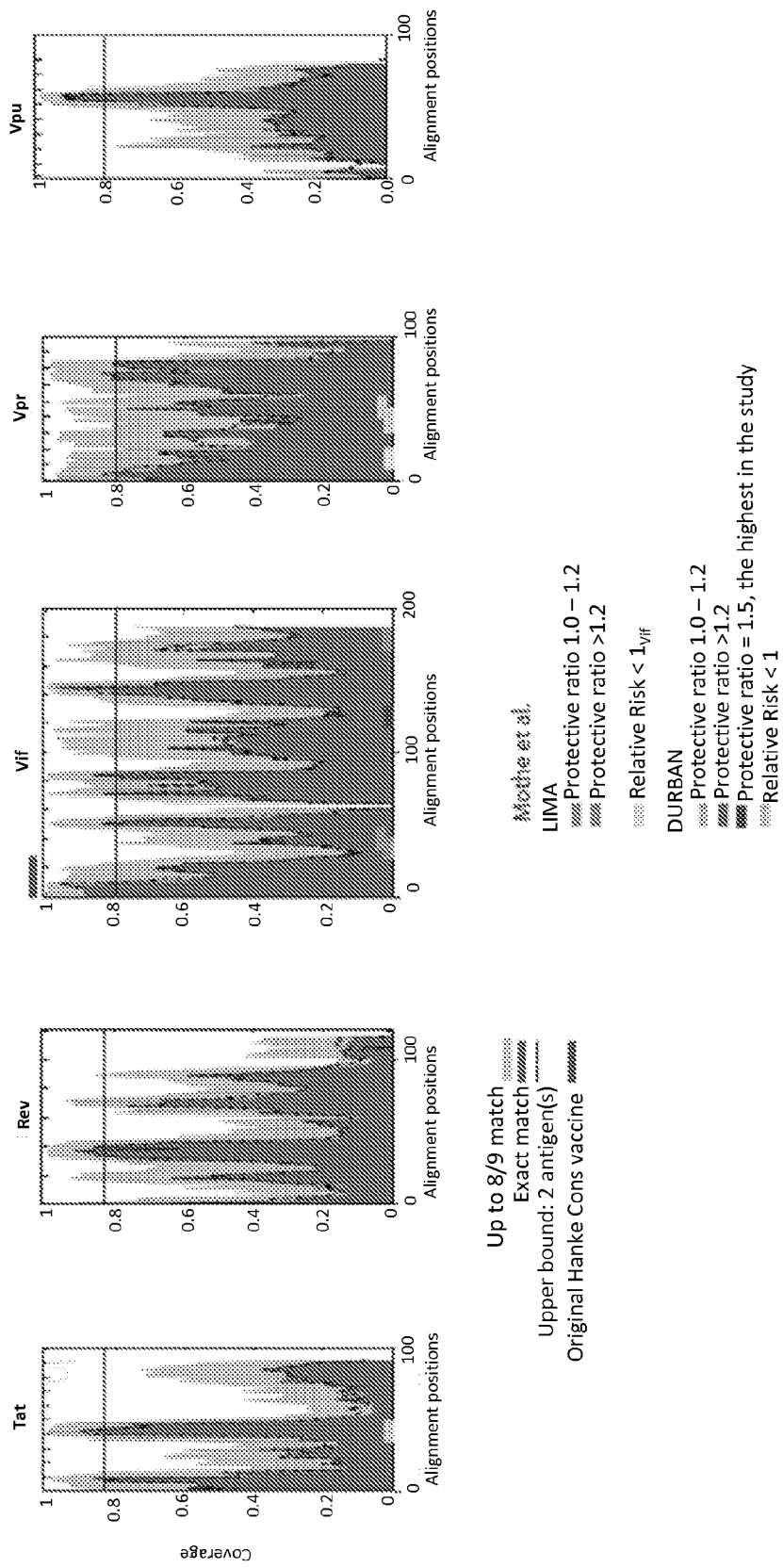
Figure 2B:
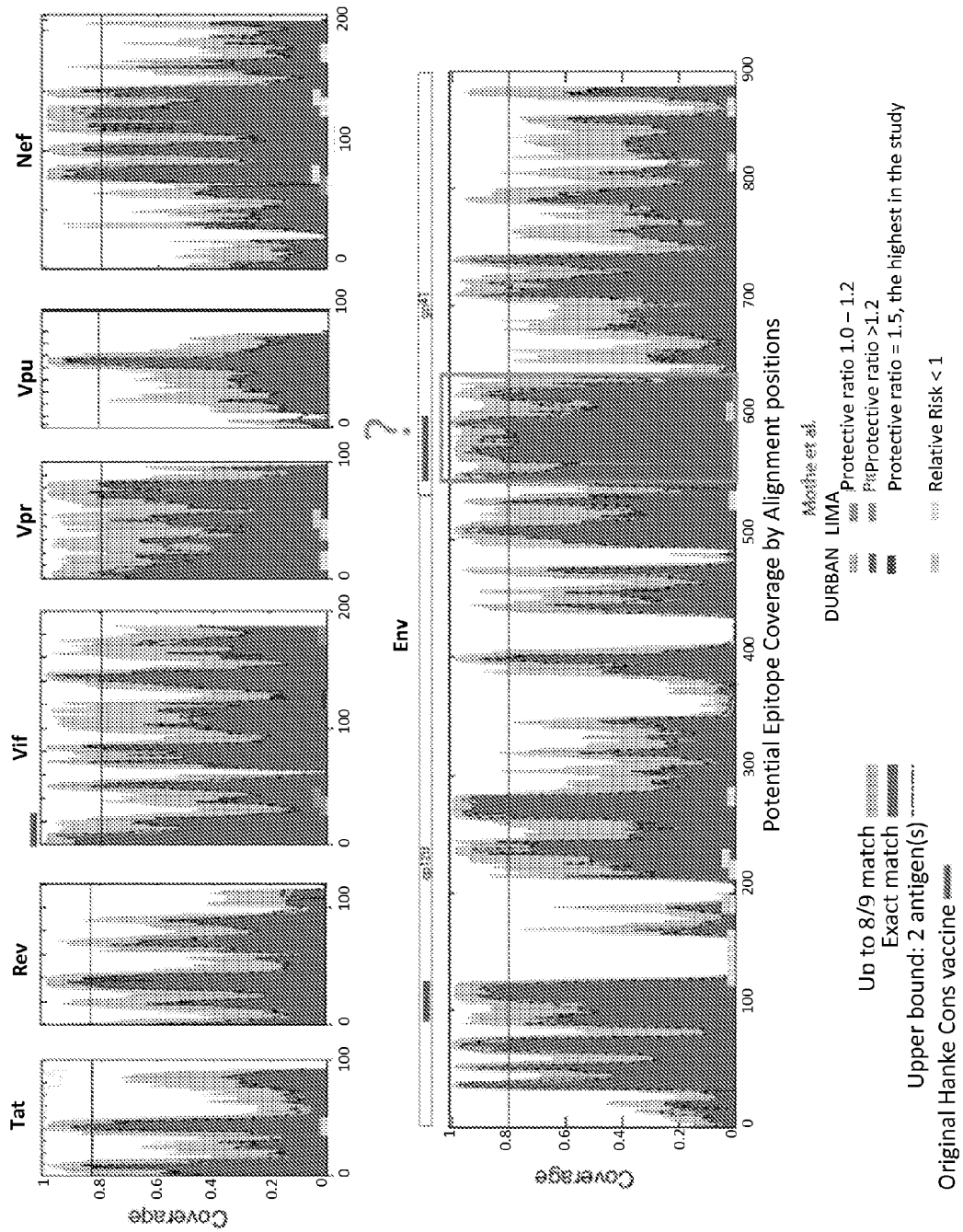
Figure 3A:
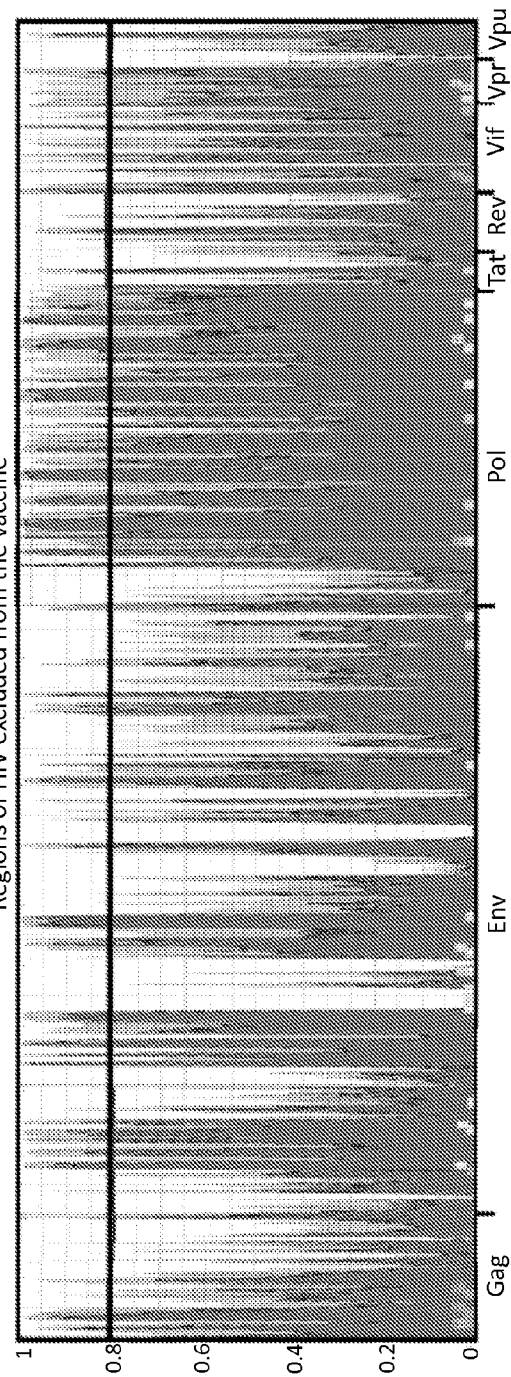
Figure 3B:
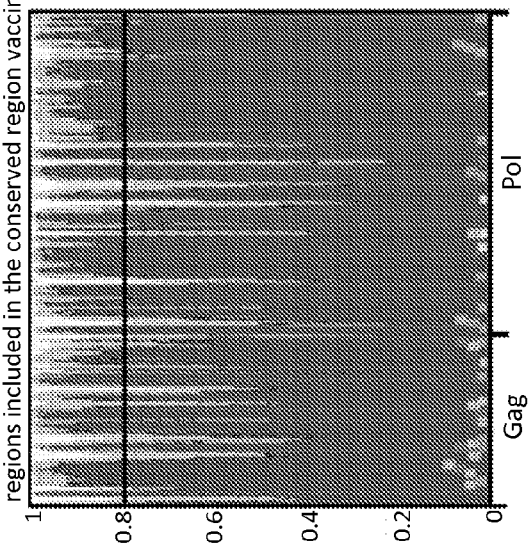
Figure 3B:
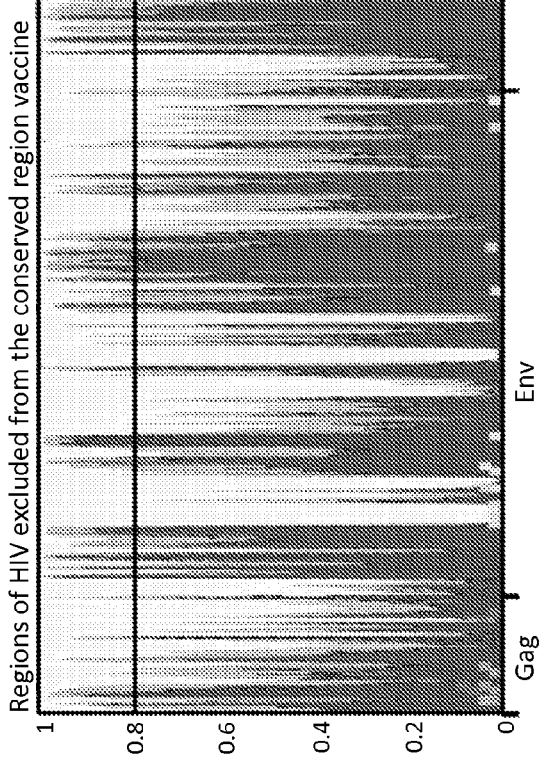
Figure 4A:
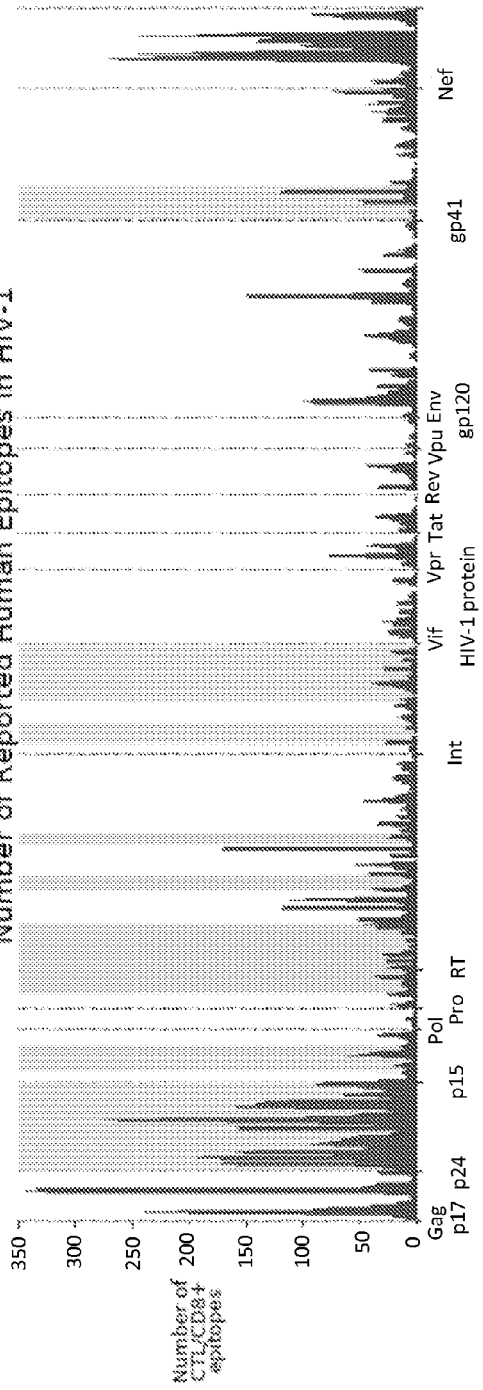
Figure 4A:
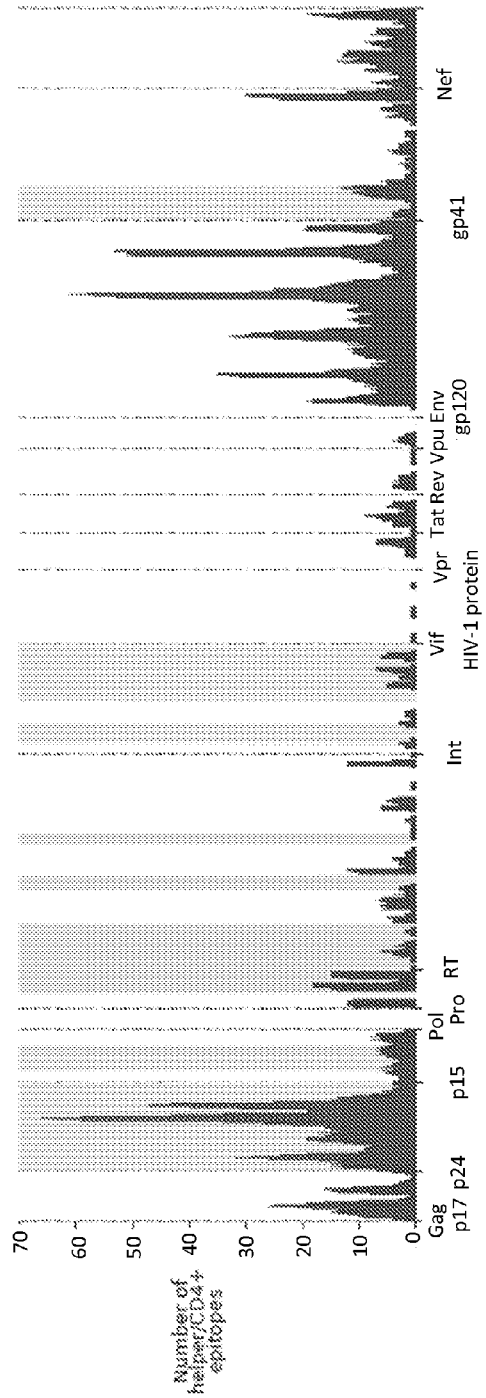
Figure 4B:
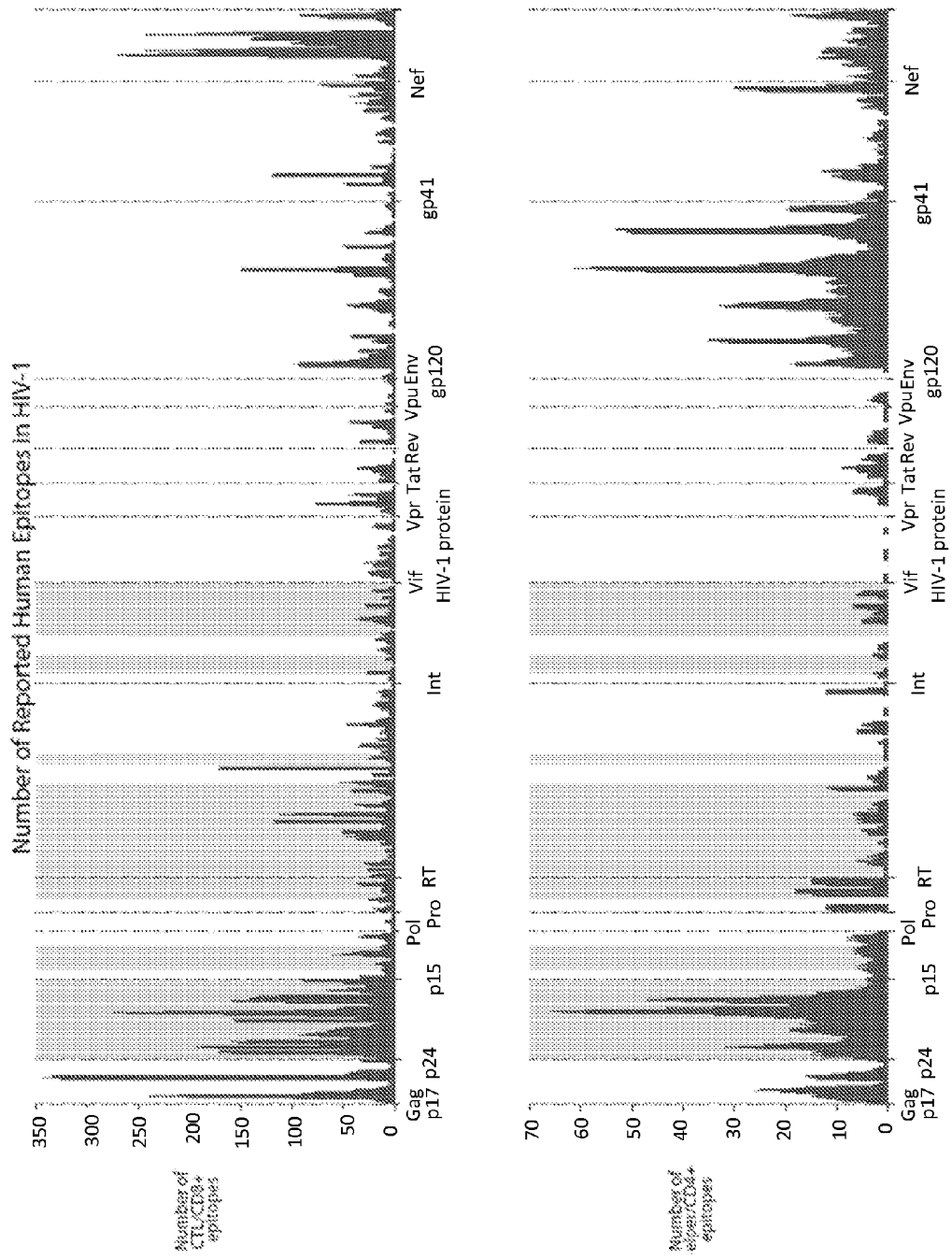

ing administering to the subject at least one of the disclosed immunogenic polypeptides or a nucleic acid encoding at least one of the immunogenic polypeptides.

20 Claims, 8 Drawing Sheets

(56) References Cited

U.S. PATENT DOCUMENTS

2011/0305749 A1  12/2011  Duch et al.
2012/0231028 A1   9/2012  Korber et al.

OTHER PUBLICATIONS

Gupta and Siber Adjuvants for human vaccines-current status, problems and future prospects. Vaccine, 19995; 13(14): 1263-1276.*

GENBANK Accession No. ACI03530, Jul. 23, 2009 (1 page).
Barouch et al., "Mosaic HIV-1 Vaccines Expand the Breadth and Depth of Cellular Immune Responses in Rhesus Monkeys," *Nat. Med.*, vol. 16, pp. 319-323, 2010 (15 pages, author manuscript version).
Fischer et al., "Polyvalent vaccines for optimal coverage of potential T-cell epitopes in global HIV-1 variants," *Nature Medicine*, vol. 13, No. 1, pp. 100-106 (2007).
Hanke et al., "HIV-1: From escapism to conservatism," *Eur. J. Immunol.*, vol. 41, pp. 3390-3393, 2011.
Letourneau et al., "Design and Pre-Clinical Evaluation of a Universal HIV-1 Vaccine," *PLoS One*, vol. 2, e984, 2007 (11 pages).
Santra et al. "Mosaic Vaccines Elicit CD8+ T lymphocyte Responses in Monkeys that Confer Enhanced Immune Coverage of Diverse HIV Strains," *Nat. Med.*, vol. 16, pp. 324-328, 2010 (13 pages, author manuscript version).
UniProtKB/TrEMBL C4MJI7 9HIV1, Feb. 8, 2011 (1 page).
UniProtKB/TrEMBL, Accession No. M4TF15_9HIV1, Jul. 24, 2014 (1 page).

* cited by examiner

Positional coverage of 9 mers among M group proteins in the 2013 database, by the 2 mosaic vaccines design

SEQUENCE LISTING

```
<160> NUMBER OF SEQ ID NOS: 39

<210> SEQ ID NO 1
<211> LENGTH: 86
<212> TYPE: PRT
<213> ORGANISM: Artificial Sequence
<220> FEATURE:
<223> OTHER INFORMATION: Mos.Env.2.1.516-601 peptide

<400> SEQUENCE: 1

Gly Phe Leu Gly Ala Ala Gly Ser Thr Met Gly Ala Ala Ser Ile Thr
1               5                   10                  15

Leu Thr Val Gln Ala Arg Leu Leu Leu Ser Gly Ile Val Gln Gln Gln
            20                  25                  30

Asn Asn Leu Leu Arg Ala Ile Glu Ala Gln Gln His Leu Leu Gln Leu
        35                  40                  45

Thr Val Trp Gly Ile Lys Gln Leu Gln Ala Arg Val Leu Ala Val Glu
    50                  55                  60

Arg Tyr Leu Lys Asp Gln Gln Leu Leu Gly Ile Trp Gly Cys Ser Gly
65                  70                  75                  80

Lys Leu Ile Cys Thr Thr
                85

<210> SEQ ID NO 2
<211> LENGTH: 231
<212> TYPE: PRT
<213> ORGANISM: Artificial Sequence
<220> FEATURE:
<223> OTHER INFORMATION: Mos.Gag.2.1.133-363 peptide
```

<400> SEQUENCE: 2

Pro Ile Val Gln Asn Leu Gln Gly Gln Met Val His Gln Ala Ile Ser
1               5                   10                  15

Pro Arg Thr Leu Asn Ala Trp Val Lys Val Ile Glu Glu Lys Ala Phe
            20                  25                  30

Ser Pro Glu Val Ile Pro Met Phe Thr Ala Leu Ser Glu Gly Ala Thr
        35                  40                  45

Pro Gln Asp Leu Asn Thr Met Leu Asn Thr Val Gly Gly His Gln Ala
    50                  55                  60

Ala Met Gln Met Leu Lys Asp Thr Ile Asn Glu Glu Ala Ala Glu Trp
65                  70                  75                  80

Asp Arg Val His Pro Val His Ala Gly Pro Ile Ala Pro Gly Gln Met
                85                  90                  95

Arg Glu Pro Arg Gly Ser Asp Ile Ala Gly Thr Thr Ser Asn Leu Gln
            100                 105                 110

Glu Gln Ile Gly Trp Met Thr Ser Asn Pro Pro Ile Pro Val Gly Asp
        115                 120                 125

Ile Tyr Lys Arg Trp Ile Ile Leu Gly Leu Asn Lys Ile Val Arg Met
    130                 135                 140

Tyr Ser Pro Val Ser Ile Leu Asp Ile Arg Gln Gly Pro Lys Glu Pro
145                 150                 155                 160

Phe Arg Asp Tyr Val Asp Arg Phe Phe Lys Thr Leu Arg Ala Glu Gln
                165                 170                 175

Ala Thr Gln Glu Val Lys Asn Trp Met Thr Asp Thr Leu Leu Val Gln
            180                 185                 190

Asn Ala Asn Pro Asp Cys Lys Thr Ile Leu Arg Ala Leu Gly Pro Gly
        195                 200                 205

Ala Thr Leu Glu Glu Met Met Thr Ala Cys Gln Gly Val Gly Gly Pro
    210                 215                 220

Gly His Lys Ala Arg Val Leu
225                 230

<210> SEQ ID NO 3
<211> LENGTH: 69
<212> TYPE: PRT
<213> ORGANISM: Artificial Sequence
<220> FEATURE:
<223> OTHER INFORMATION: Mos.Gag.2.1.391-459

<400> SEQUENCE: 3

Lys Cys Phe Asn Cys Gly Lys Glu Gly His Ile Ala Lys Asn Cys Arg
1               5                   10                  15

Ala Pro Arg Lys Arg Gly Cys Trp Lys Cys Gly Arg Glu Gly His Gln
            20                  25                  30

Met Lys Asp Cys Asn Glu Arg Gln Ala Asn Phe Leu Gly Lys Ile Trp
        35                  40                  45

Pro Ser His Lys Gly Arg Pro Gly Asn Phe Leu Gln Ser Arg Pro Glu
    50                  55                  60

Pro Thr Ala Pro Pro
65

<210> SEQ ID NO 4
<211> LENGTH: 182
<212> TYPE: PRT
<213> ORGANISM: Artificial Sequence
<220> FEATURE:

<223> OTHER INFORMATION: Mos.Pol.2.1.94-275 peptide

<400> SEQUENCE: 4

```
Leu Pro Gly Lys Trp Lys Pro Lys Met Ile Gly Gly Ile Gly Gly Phe
1               5                   10                  15

Ile Lys Val Lys Gln Tyr Asp Gln Ile Leu Ile Glu Ile Cys Gly Lys
            20                  25                  30

Lys Ala Ile Gly Thr Val Leu Val Gly Pro Thr Pro Val Asn Ile Ile
        35                  40                  45

Gly Arg Asn Met Leu Thr Gln Leu Gly Cys Thr Leu Asn Phe Pro Ile
    50                  55                  60

Ser Pro Ile Asp Thr Val Pro Val Thr Leu Lys Pro Gly Met Asp Gly
65                  70                  75                  80

Pro Arg Val Lys Gln Trp Pro Leu Thr Glu Glu Lys Ile Lys Ala Leu
                85                  90                  95

Thr Glu Ile Cys Lys Glu Met Glu Lys Glu Gly Lys Ile Thr Lys Ile
            100                 105                 110

Gly Pro Glu Asn Pro Tyr Asn Thr Pro Ile Phe Ala Ile Lys Lys Lys
        115                 120                 125

Asp Ser Thr Lys Trp Arg Lys Leu Val Asp Phe Arg Glu Leu Asn Lys
130                 135                 140

Lys Thr Gln Asp Phe Trp Glu Val Gln Leu Gly Ile Pro His Pro Ala
145                 150                 155                 160

Gly Leu Lys Lys Lys Ser Val Thr Val Leu Asp Val Gly Asp Ala
                165                 170                 175

Tyr Phe Ser Val Pro Leu
            180
```

<210> SEQ ID NO 5
<211> LENGTH: 37
<212> TYPE: PRT
<213> ORGANISM: Artificial Sequence
<220> FEATURE:
<223> OTHER INFORMATION: Mos.Pol.2.1.363-399 peptide

<400> SEQUENCE: 5

```
His Leu Leu Lys Trp Gly Phe Thr Thr Pro Asp Lys Lys His Gln Lys
1               5                   10                  15

Glu Pro Pro Phe Leu Trp Met Gly Tyr Glu Leu His Pro Asp Arg Trp
            20                  25                  30

Thr Val Gln Pro Ile
        35
```

<210> SEQ ID NO 6
<211> LENGTH: 29
<212> TYPE: PRT
<213> ORGANISM: Artificial Sequence
<220> FEATURE:
<223> OTHER INFORMATION: Mos.Pol.2.1.482-510 peptide

<400> SEQUENCE: 6

```
Ala Glu Ile Gln Lys Gln Gly Gln Asp Gln Trp Thr Tyr Gln Ile Tyr
1               5                   10                  15

Gln Glu Pro Phe Lys Asn Leu Lys Thr Gly Lys Tyr Ala
            20                  25
```

<210> SEQ ID NO 7
<211> LENGTH: 58
<212> TYPE: PRT

```
<213> ORGANISM: Artificial Sequence
<220> FEATURE:
<223> OTHER INFORMATION: Mos.Pol.2.1.741-798 peptide

<400> SEQUENCE: 7

Phe Asn Leu Pro Pro Ile Val Ala Lys Glu Ile Val Ala Asn Cys Asp
1               5                   10                  15

Lys Cys Gln Leu Lys Gly Glu Ala Met His Gly Gln Val Asp Cys Ser
            20                  25                  30

Pro Gly Ile Trp Gln Leu Asp Cys Thr His Leu Glu Gly Lys Val Ile
        35                  40                  45

Leu Val Ala Val His Val Ala Ser Gly Tyr
    50                  55

<210> SEQ ID NO 8
<211> LENGTH: 152
<212> TYPE: PRT
<213> ORGANISM: Artificial Sequence
<220> FEATURE:
<223> OTHER INFORMATION: Mos.Pol.2.1.852-1003 peptide

<400> SEQUENCE: 8

Gln Glu Phe Gly Ile Pro Tyr Asn Pro Gln Ser Gln Gly Val Val Glu
1               5                   10                  15

Ser Met Asn Lys Glu Leu Lys Lys Ile Ile Gly Gln Val Arg Glu Gln
            20                  25                  30

Ala Glu His Leu Lys Thr Ala Val Gln Met Ala Val Phe Ile His Asn
        35                  40                  45

Phe Lys Arg Lys Gly Gly Ile Gly Gly Tyr Ser Ala Gly Glu Arg Ile
    50                  55                  60

Ile Asp Ile Ile Ala Thr Asp Ile Gln Thr Lys Glu Leu Gln Lys Gln
65                  70                  75                  80

Ile Thr Lys Ile Gln Asn Phe Arg Val Tyr Tyr Arg Asp Ser Arg Asp
                85                  90                  95

Pro Ile Trp Lys Gly Pro Ala Lys Leu Leu Trp Lys Gly Glu Gly Ala
            100                 105                 110

Val Val Ile Gln Asp Asn Ser Asp Ile Lys Val Val Pro Arg Arg Lys
        115                 120                 125

Val Lys Ile Ile Lys Asp Tyr Gly Lys Gln Met Ala Gly Ala Asp Cys
    130                 135                 140

Val Ala Gly Arg Gln Asp Glu Asp
145                 150

<210> SEQ ID NO 9
<211> LENGTH: 86
<212> TYPE: PRT
<213> ORGANISM: Artificial Sequence
<220> FEATURE:
<223> OTHER INFORMATION: Mos.Env.2.2.516-601 peptide

<400> SEQUENCE: 9

Gly Phe Leu Gly Ala Ala Gly Ser Thr Met Gly Ala Ala Ser Leu Thr
1               5                   10                  15

Leu Thr Val Gln Ala Arg Gln Leu Leu Ser Gly Ile Val Gln Gln Gln
            20                  25                  30

Ser Asn Leu Leu Arg Ala Ile Glu Ala Gln Gln His Met Leu Gln Leu
        35                  40                  45

Thr Val Trp Gly Ile Lys Gln Leu Gln Thr Arg Val Leu Ala Ile Glu
    50                  55                  60
```

```
Arg Tyr Leu Lys Asp Gln Gln Leu Leu Gly Leu Trp Gly Cys Ser Gly
 65                  70                  75                  80

Lys Leu Ile Cys Thr Thr
                 85

<210> SEQ ID NO 10
<211> LENGTH: 231
<212> TYPE: PRT
<213> ORGANISM: Artificial Sequence
<220> FEATURE:
<223> OTHER INFORMATION: Mos.Gag.2.2.133-363 peptide

<400> SEQUENCE: 10

Pro Ile Val Gln Asn Ala Gln Gly Gln Met Val His Gln Ala Leu Ser
  1               5                  10                  15

Pro Arg Thr Leu Asn Ala Trp Val Lys Val Val Glu Glu Lys Ala Phe
             20                  25                  30

Ser Pro Glu Val Ile Pro Met Phe Ser Ala Leu Ser Glu Gly Ala Thr
         35                  40                  45

Pro Gln Asp Leu Asn Met Met Leu Asn Ile Val Gly Gly His Gln Ala
     50                  55                  60

Ala Met Gln Met Leu Lys Glu Thr Ile Asn Glu Glu Ala Ala Glu Trp
 65                  70                  75                  80

Asp Arg Leu His Pro Val His Ala Gly Pro Ile Pro Pro Gly Gln Met
                 85                  90                  95

Arg Glu Pro Arg Gly Ser Asp Ile Ala Gly Thr Thr Ser Thr Leu Gln
            100                 105                 110

Glu Gln Ile Gly Trp Met Thr Asn Asn Pro Pro Ile Pro Val Gly Glu
        115                 120                 125

Ile Tyr Lys Arg Trp Ile Ile Met Gly Leu Asn Lys Ile Val Arg Met
    130                 135                 140

Tyr Ser Pro Thr Ser Ile Leu Asp Ile Lys Gln Gly Pro Lys Glu Pro
145                 150                 155                 160

Phe Arg Asp Tyr Val Asp Arg Phe Tyr Lys Thr Leu Arg Ala Glu Gln
                165                 170                 175

Ala Ser Gln Glu Val Lys Asn Trp Met Thr Glu Thr Leu Leu Val Gln
            180                 185                 190

Asn Ala Asn Pro Asp Cys Lys Thr Ile Leu Lys Ala Leu Gly Pro Ala
        195                 200                 205

Ala Thr Leu Glu Glu Met Met Thr Ala Cys Gln Gly Val Gly Gly Pro
    210                 215                 220

Ser His Lys Ala Arg Val Leu
225                 230

<210> SEQ ID NO 11
<211> LENGTH: 69
<212> TYPE: PRT
<213> ORGANISM: Artificial Sequence
<220> FEATURE:
<223> OTHER INFORMATION: Mos.Gag.2.2.391-459 peptide

<400> SEQUENCE: 11

Lys Cys Phe Asn Cys Gly Lys Glu Gly His Leu Ala Arg Asn Cys Arg
  1               5                  10                  15

Ala Pro Arg Lys Lys Gly Cys Trp Lys Cys Gly Lys Glu Gly His Gln
             20                  25                  30

Met Lys Asp Cys Thr Glu Arg Gln Ala Asn Phe Leu Gly Lys Ile Trp
```

```
                35                  40                  45
Pro Ser Asn Lys Gly Arg Pro Gly Asn Phe Pro Gln Ser Arg Pro Glu
    50                  55                  60

Pro Ser Ala Pro Pro
65

<210> SEQ ID NO 12
<211> LENGTH: 182
<212> TYPE: PRT
<213> ORGANISM: Artificial Sequence
<220> FEATURE:
<223> OTHER INFORMATION: Mos.Pol.2.2.94-275 peptide

<400> SEQUENCE: 12

Leu Pro Gly Arg Trp Lys Pro Lys Met Ile Gly Gly Ile Gly Gly Phe
1               5                   10                  15

Ile Lys Val Arg Gln Tyr Asp Gln Ile Pro Ile Glu Ile Cys Gly His
            20                  25                  30

Lys Ala Ile Gly Thr Val Leu Ile Gly Pro Thr Pro Val Asn Ile Ile
        35                  40                  45

Gly Arg Asn Leu Leu Thr Gln Ile Gly Cys Thr Leu Asn Phe Pro Ile
    50                  55                  60

Ser Pro Ile Glu Thr Val Pro Val Lys Leu Lys Pro Gly Met Asp Gly
65                  70                  75                  80

Pro Lys Val Lys Gln Trp Pro Leu Thr Glu Glu Lys Ile Lys Ala Leu
                85                  90                  95

Val Glu Ile Cys Thr Glu Met Glu Lys Glu Gly Lys Ile Ser Lys Ile
            100                 105                 110

Gly Pro Glu Asn Pro Tyr Asn Thr Pro Val Phe Ala Ile Lys Lys Lys
        115                 120                 125

Asp Ser Thr Arg Trp Arg Lys Leu Val Asp Phe Arg Glu Leu Asn Lys
    130                 135                 140

Arg Thr Gln Asp Phe Trp Glu Val Gln Leu Gly Ile Pro His Pro Ser
145                 150                 155                 160

Gly Leu Lys Lys Lys Arg Ser Val Thr Val Leu Asp Val Gly Asp Ala
                165                 170                 175

Tyr Phe Ser Val Pro Leu
            180

<210> SEQ ID NO 13
<211> LENGTH: 37
<212> TYPE: PRT
<213> ORGANISM: Artificial Sequence
<220> FEATURE:
<223> OTHER INFORMATION: Mos.Pol.2.2.363-399 peptide

<400> SEQUENCE: 13

His Leu Leu Arg Trp Gly Phe Thr Thr Pro Asp Lys Lys His Gln Lys
1               5                   10                  15

Glu Pro Pro Phe His Trp Met Gly Tyr Glu Leu His Pro Asp Lys Trp
            20                  25                  30

Thr Val Gln Pro Ile
        35

<210> SEQ ID NO 14
<211> LENGTH: 29
<212> TYPE: PRT
<213> ORGANISM: Artificial Sequence
<220> FEATURE:
```

<223> OTHER INFORMATION: Mos.Pol.2.2.482-510 peptide

<400> SEQUENCE: 14

Ala Glu Ile Gln Lys Gln Gly Gln Gly Gln Trp Thr Tyr Gln Ile Tyr
1               5                   10                  15

Gln Glu Pro Tyr Lys Asn Leu Lys Thr Gly Lys Tyr Ala
            20                  25

<210> SEQ ID NO 15
<211> LENGTH: 58
<212> TYPE: PRT
<213> ORGANISM: Artificial Sequence
<220> FEATURE:
<223> OTHER INFORMATION: Mos.Pol.2.2.741-798 peptide

<400> SEQUENCE: 15

Phe Asn Leu Pro Pro Val Val Ala Lys Glu Ile Val Ala Ser Cys Asp
1               5                   10                  15

Lys Cys Gln Leu Lys Gly Glu Ala Ile His Gly Gln Val Asp Cys Ser
            20                  25                  30

Pro Gly Met Trp Gln Leu Asp Cys Thr His Leu Glu Gly Lys Ile Ile
        35                  40                  45

Leu Val Ala Val His Val Ala Ser Gly Tyr
        50                  55

<210> SEQ ID NO 16
<211> LENGTH: 152
<212> TYPE: PRT
<213> ORGANISM: Artificial Sequence
<220> FEATURE:
<223> OTHER INFORMATION: Mos.Pol.2.2.852-1003 peptide

<400> SEQUENCE: 16

Gln Glu Phe Gly Ile Pro Tyr Asn Pro Gln Ser Gln Gly Val Val Glu
1               5                   10                  15

Ser Met Asn Asn Glu Leu Lys Lys Ile Ile Gly Gln Val Arg Asp Gln
            20                  25                  30

Ala Glu His Leu Lys Thr Ala Val Gln Met Ala Val Leu Ile His Asn
        35                  40                  45

Phe Lys Arg Arg Gly Gly Ile Gly Gly Tyr Ser Ala Gly Glu Arg Ile
    50                  55                  60

Val Asp Ile Ile Ala Thr Asp Ile Gln Thr Arg Glu Leu Gln Lys Gln
65                  70                  75                  80

Ile Ile Lys Ile Gln Asn Phe Arg Val Tyr Tyr Arg Asp Ser Arg Asp
                85                  90                  95

Pro Leu Trp Lys Gly Pro Ala Lys Leu Leu Trp Arg Gly Glu Gly Ala
            100                 105                 110

Val Val Ile Gln Asp Asn Ser Glu Ile Lys Val Val Pro Arg Arg Lys
        115                 120                 125

Ala Lys Ile Ile Arg Asp Tyr Gly Lys Gln Met Ala Gly Asp Asp Cys
    130                 135                 140

Val Ala Ser Arg Gln Asp Glu Asp
145                 150

<210> SEQ ID NO 17
<211> LENGTH: 333
<212> TYPE: PRT
<213> ORGANISM: Artificial Sequence
<220> FEATURE:
<223> OTHER INFORMATION: Mos.Pol.2.1.94-426 peptide

<400> SEQUENCE: 17

```
Leu Pro Gly Lys Trp Lys Pro Lys Met Ile Gly Gly Ile Gly Gly Phe
1               5                   10                  15

Ile Lys Val Lys Gln Tyr Asp Gln Ile Leu Ile Glu Ile Cys Gly Lys
            20                  25                  30

Lys Ala Ile Gly Thr Val Leu Val Gly Pro Thr Pro Val Asn Ile Ile
        35                  40                  45

Gly Arg Asn Met Leu Thr Gln Leu Gly Cys Thr Leu Asn Phe Pro Ile
    50                  55                  60

Ser Pro Ile Asp Thr Val Pro Val Thr Leu Lys Pro Gly Met Asp Gly
65                  70                  75                  80

Pro Arg Val Lys Gln Trp Pro Leu Thr Glu Glu Lys Ile Lys Ala Leu
                85                  90                  95

Thr Glu Ile Cys Lys Glu Met Glu Lys Glu Gly Lys Ile Thr Lys Ile
            100                 105                 110

Gly Pro Glu Asn Pro Tyr Asn Thr Pro Ile Phe Ala Ile Lys Lys Lys
        115                 120                 125

Asp Ser Thr Lys Trp Arg Lys Leu Val Asp Phe Arg Glu Leu Asn Lys
130                 135                 140

Lys Thr Gln Asp Phe Trp Glu Val Gln Leu Gly Ile Pro His Pro Ala
145                 150                 155                 160

Gly Leu Lys Lys Lys Ser Val Thr Val Leu Asp Val Gly Asp Ala
                165                 170                 175

Tyr Phe Ser Val Pro Leu Asp Glu Ser Phe Arg Lys Tyr Thr Ala Phe
            180                 185                 190

Thr Ile Pro Ser Ile Asn Asn Glu Thr Pro Gly Ile Arg Tyr Gln Tyr
        195                 200                 205

Asn Val Leu Pro Gln Gly Trp Lys Gly Ser Pro Ala Ile Phe Gln Ser
    210                 215                 220

Ser Met Thr Lys Ile Leu Glu Pro Phe Arg Ala Lys Asn Pro Glu Ile
225                 230                 235                 240

Val Ile Tyr Gln Tyr Met Asp Asp Leu Tyr Val Gly Ser Asp Leu Glu
                245                 250                 255

Ile Gly Gln His Arg Ala Lys Ile Glu Glu Leu Arg Glu His Leu Leu
            260                 265                 270

Lys Trp Gly Phe Thr Thr Pro Asp Lys Lys His Gln Lys Glu Pro Pro
        275                 280                 285

Phe Leu Trp Met Gly Tyr Glu Leu His Pro Asp Arg Trp Thr Val Gln
    290                 295                 300

Pro Ile Gln Leu Pro Glu Lys Glu Ser Trp Thr Val Asn Asp Ile Gln
305                 310                 315                 320

Lys Leu Ile Gly Lys Leu Asn Trp Ala Ser Gln Ile Tyr
                325                 330
```

<210> SEQ ID NO 18
<211> LENGTH: 333
<212> TYPE: PRT
<213> ORGANISM: Artificial Sequence
<220> FEATURE:
<223> OTHER INFORMATION: Mos.Pol.2.2.94-426 peptide

<400> SEQUENCE: 18

```
Leu Pro Gly Arg Trp Lys Pro Lys Met Ile Gly Gly Ile Gly Gly Phe
1               5                   10                  15
```

Ile Lys Val Arg Gln Tyr Asp Gln Ile Pro Ile Glu Ile Cys Gly His
            20                  25                  30

Lys Ala Ile Gly Thr Val Leu Ile Gly Pro Thr Pro Val Asn Ile Ile
        35                  40                  45

Gly Arg Asn Leu Leu Thr Gln Ile Gly Cys Thr Leu Asn Phe Pro Ile
    50                  55                  60

Ser Pro Ile Glu Thr Val Pro Val Lys Leu Lys Pro Gly Met Asp Gly
65                  70                  75                  80

Pro Lys Val Lys Gln Trp Pro Leu Thr Glu Glu Lys Ile Lys Ala Leu
                85                  90                  95

Val Glu Ile Cys Thr Glu Met Glu Lys Glu Gly Lys Ile Ser Lys Ile
            100                 105                 110

Gly Pro Glu Asn Pro Tyr Asn Thr Pro Val Phe Ala Ile Lys Lys Lys
        115                 120                 125

Asp Ser Thr Arg Trp Arg Lys Leu Val Asp Phe Arg Glu Leu Asn Lys
    130                 135                 140

Arg Thr Gln Asp Phe Trp Glu Val Gln Leu Gly Ile Pro His Pro Ser
145                 150                 155                 160

Gly Leu Lys Lys Lys Arg Ser Val Thr Val Leu Asp Val Gly Asp Ala
                165                 170                 175

Tyr Phe Ser Val Pro Leu Asp Lys Asp Phe Arg Lys Tyr Thr Ala Phe
            180                 185                 190

Thr Ile Pro Ser Thr Asn Asn Glu Thr Pro Gly Val Arg Tyr Gln Tyr
        195                 200                 205

Asn Val Leu Pro Met Gly Trp Lys Gly Ser Pro Ala Ile Phe Gln Cys
    210                 215                 220

Ser Met Thr Lys Ile Leu Glu Pro Phe Arg Lys Gln Asn Pro Asp Ile
225                 230                 235                 240

Val Ile Tyr Gln Tyr Met Asp Asp Leu Tyr Ile Gly Ser Asp Leu Glu
                245                 250                 255

Ile Gly Gln His Arg Thr Lys Ile Glu Glu Leu Arg Gln His Leu Leu
            260                 265                 270

Arg Trp Gly Phe Thr Thr Pro Asp Lys Lys His Gln Lys Glu Pro Pro
        275                 280                 285

Phe His Trp Met Gly Tyr Glu Leu His Pro Asp Lys Trp Thr Val Gln
    290                 295                 300

Pro Ile Val Leu Pro Glu Lys Asp Ser Trp Thr Val Asn Asp Ile Gln
305                 310                 315                 320

Lys Leu Val Gly Lys Leu Asn Trp Ala Ser Gln Ile Tyr
                325                 330

<210> SEQ ID NO 19
<211> LENGTH: 16
<212> TYPE: PRT
<213> ORGANISM: Artificial Sequence
<220> FEATURE:
<223> OTHER INFORMATION: Pol peptide

<400> SEQUENCE: 19

Lys Asn Pro Glu Ile Val Ile Tyr Gln Tyr Met Asp Asp Leu Tyr Val
1               5                   10                  15

<210> SEQ ID NO 20
<211> LENGTH: 15
<212> TYPE: PRT
<213> ORGANISM: Artificial Sequence
<220> FEATURE:

-continued

<223> OTHER INFORMATION: Pol peptide

<400> SEQUENCE: 20

Val Ile Tyr Gln Tyr Met Asp Asp Leu Tyr Val Gly Ser Asp Leu
1               5                   10                  15

<210> SEQ ID NO 21
<211> LENGTH: 23
<212> TYPE: PRT
<213> ORGANISM: Artificial Sequence
<220> FEATURE:
<223> OTHER INFORMATION: tPA leader peptide

<400> SEQUENCE: 21

Met Asp Ala Met Lys Arg Gly Leu Cys Cys Val Leu Leu Leu Cys Gly
1               5                   10                  15

Ala Val Phe Val Ser Ala Arg
            20

<210> SEQ ID NO 22
<211> LENGTH: 86
<212> TYPE: PRT
<213> ORGANISM: Artificial Sequence
<220> FEATURE:
<223> OTHER INFORMATION: HXB2.516-601 peptide

<400> SEQUENCE: 22

Gly Phe Leu Gly Ala Ala Gly Ser Thr Met Gly Ala Ala Ser Met Thr
1               5                   10                  15

Leu Thr Val Gln Ala Arg Gln Leu Leu Ser Gly Ile Val Gln Gln Gln
            20                  25                  30

Asn Asn Leu Leu Arg Ala Ile Glu Ala Gln Gln His Leu Leu Gln Leu
        35                  40                  45

Thr Val Trp Gly Ile Lys Gln Leu Gln Ala Arg Ile Leu Ala Val Glu
    50                  55                  60

Arg Tyr Leu Lys Asp Gln Gln Leu Leu Gly Ile Trp Gly Cys Ser Gly
65                  70                  75                  80

Lys Leu Ile Cys Thr Thr
                85

<210> SEQ ID NO 23
<211> LENGTH: 231
<212> TYPE: PRT
<213> ORGANISM: Artificial Sequence
<220> FEATURE:
<223> OTHER INFORMATION: HXB2.133-363 peptide

<400> SEQUENCE: 23

Pro Ile Val Gln Asn Ile Gln Gly Gln Met Val His Gln Ala Ile Ser
1               5                   10                  15

Pro Arg Thr Leu Asn Ala Trp Val Lys Val Val Glu Glu Lys Ala Phe
            20                  25                  30

Ser Pro Glu Val Ile Pro Met Phe Ser Ala Leu Ser Glu Gly Ala Thr
        35                  40                  45

Pro Gln Asp Leu Asn Thr Met Leu Asn Thr Val Gly Gly His Gln Ala
    50                  55                  60

Ala Met Gln Met Leu Lys Glu Thr Ile Asn Glu Glu Ala Ala Glu Trp
65                  70                  75                  80

Asp Arg Val His Pro Val His Ala Gly Pro Ile Ala Pro Gly Gln Met
                85                  90                  95

```
Arg Glu Pro Arg Gly Ser Asp Ile Ala Gly Thr Thr Ser Thr Leu Gln
            100                 105                 110

Glu Gln Ile Gly Trp Met Thr Asn Asn Pro Pro Ile Pro Val Gly Glu
        115                 120                 125

Ile Tyr Lys Arg Trp Ile Ile Leu Gly Leu Asn Lys Ile Val Arg Met
    130                 135                 140

Tyr Ser Pro Thr Ser Ile Leu Asp Ile Arg Gln Gly Pro Lys Glu Pro
145                 150                 155                 160

Phe Arg Asp Tyr Val Asp Arg Phe Tyr Lys Thr Leu Arg Ala Glu Gln
                165                 170                 175

Ala Ser Gln Glu Val Lys Asn Trp Met Thr Glu Thr Leu Leu Val Gln
            180                 185                 190

Asn Ala Asn Pro Asp Cys Lys Thr Ile Leu Lys Ala Leu Gly Pro Ala
        195                 200                 205

Ala Thr Leu Glu Glu Met Met Thr Ala Cys Gln Gly Val Gly Gly Pro
    210                 215                 220

Gly His Lys Ala Arg Val Leu
225                 230

<210> SEQ ID NO 24
<211> LENGTH: 69
<212> TYPE: PRT
<213> ORGANISM: Artificial Sequence
<220> FEATURE:
<223> OTHER INFORMATION: HXB2.Gag.391-459 peptide

<400> SEQUENCE: 24

Lys Cys Phe Asn Cys Gly Lys Glu Gly His Thr Ala Arg Asn Cys Arg
1               5                   10                  15

Ala Pro Arg Lys Lys Gly Cys Trp Lys Cys Gly Lys Glu Gly His Gln
            20                  25                  30

Met Lys Asp Cys Thr Glu Arg Gln Ala Asn Phe Leu Gly Lys Ile Trp
        35                  40                  45

Pro Ser Tyr Lys Gly Arg Pro Gly Asn Phe Leu Gln Ser Arg Pro Glu
    50                  55                  60

Pro Thr Ala Pro Pro
65

<210> SEQ ID NO 25
<211> LENGTH: 182
<212> TYPE: PRT
<213> ORGANISM: Artificial Sequence
<220> FEATURE:
<223> OTHER INFORMATION: HXB2.Pol.94-275 peptide

<400> SEQUENCE: 25

Leu Pro Gly Arg Trp Lys Pro Lys Met Ile Gly Gly Ile Gly Gly Phe
1               5                   10                  15

Ile Lys Val Arg Gln Tyr Asp Gln Ile Leu Ile Glu Ile Cys Gly His
            20                  25                  30

Lys Ala Ile Gly Thr Val Leu Val Gly Pro Thr Pro Val Asn Ile Ile
        35                  40                  45

Gly Arg Asn Leu Leu Thr Gln Ile Gly Cys Thr Leu Asn Phe Pro Ile
    50                  55                  60

Ser Pro Ile Glu Thr Val Pro Val Lys Leu Lys Pro Gly Met Asp Gly
65                  70                  75                  80

Pro Lys Val Lys Gln Trp Pro Leu Thr Glu Glu Lys Ile Lys Ala Leu
            85                  90                  95
```

-continued

```
Val Glu Ile Cys Thr Glu Met Glu Lys Glu Gly Lys Ile Ser Lys Ile
                100                 105                 110
Gly Pro Glu Asn Pro Tyr Asn Thr Pro Val Phe Ala Ile Lys Lys Lys
            115                 120                 125
Asp Ser Thr Lys Trp Arg Lys Leu Val Asp Phe Arg Glu Leu Asn Lys
130                 135                 140
Arg Thr Gln Asp Phe Trp Glu Val Gln Leu Gly Ile Pro His Pro Ala
145                 150                 155                 160
Gly Leu Lys Lys Lys Lys Ser Val Thr Val Leu Asp Val Gly Asp Ala
                165                 170                 175
Tyr Phe Ser Val Pro Leu
            180

<210> SEQ ID NO 26
<211> LENGTH: 37
<212> TYPE: PRT
<213> ORGANISM: Artificial Sequence
<220> FEATURE:
<223> OTHER INFORMATION: HXB2.Pol.363-399 peptide

<400> SEQUENCE: 26

His Leu Leu Arg Trp Gly Leu Thr Thr Pro Asp Lys Lys His Gln Lys
1               5                   10                  15
Glu Pro Pro Phe Leu Trp Met Gly Tyr Glu Leu His Pro Asp Lys Trp
            20                  25                  30
Thr Val Gln Pro Ile
        35

<210> SEQ ID NO 27
<211> LENGTH: 29
<212> TYPE: PRT
<213> ORGANISM: Artificial Sequence
<220> FEATURE:
<223> OTHER INFORMATION: HXB2.Pol.482-510 peptide

<400> SEQUENCE: 27

Ala Glu Ile Gln Lys Gln Gly Gln Gly Gln Trp Thr Tyr Gln Ile Tyr
1               5                   10                  15
Gln Glu Pro Phe Lys Asn Leu Lys Thr Gly Lys Tyr Ala
            20                  25

<210> SEQ ID NO 28
<211> LENGTH: 58
<212> TYPE: PRT
<213> ORGANISM: Artificial Sequence
<220> FEATURE:
<223> OTHER INFORMATION: HXB2.Pol.741-798 peptide

<400> SEQUENCE: 28

Phe Asn Leu Pro Pro Val Val Ala Lys Glu Ile Val Ala Ser Cys Asp
1               5                   10                  15
Lys Cys Gln Leu Lys Gly Glu Ala Met His Gly Gln Val Asp Cys Ser
            20                  25                  30
Pro Gly Ile Trp Gln Leu Asp Cys Thr His Leu Glu Gly Lys Val Ile
        35                  40                  45
Leu Val Ala Val His Val Ala Ser Gly Tyr
    50                  55

<210> SEQ ID NO 29
<211> LENGTH: 152
```

```
<212> TYPE: PRT
<213> ORGANISM: Artificial Sequence
<220> FEATURE:
<223> OTHER INFORMATION: HXB2.Pol.852-1003 peptide

<400> SEQUENCE: 29

Gln Glu Phe Gly Ile Pro Tyr Asn Pro Gln Ser Gln Gly Val Val Glu
1               5                   10                  15

Ser Met Asn Lys Glu Leu Lys Lys Ile Ile Gly Gln Val Arg Asp Gln
            20                  25                  30

Ala Glu His Leu Lys Thr Ala Val Gln Met Ala Val Phe Ile His Asn
        35                  40                  45

Phe Lys Arg Lys Gly Gly Ile Gly Gly Tyr Ser Ala Gly Glu Arg Ile
    50                  55                  60

Val Asp Ile Ile Ala Thr Asp Ile Gln Thr Lys Glu Leu Gln Lys Gln
65                  70                  75                  80

Ile Thr Lys Ile Gln Asn Phe Arg Val Tyr Tyr Arg Asp Ser Arg Asn
                85                  90                  95

Pro Leu Trp Lys Gly Pro Ala Lys Leu Leu Trp Lys Gly Glu Gly Ala
            100                 105                 110

Val Val Ile Gln Asp Asn Ser Asp Ile Lys Val Val Pro Arg Arg Lys
        115                 120                 125

Ala Lys Ile Ile Arg Asp Tyr Gly Lys Gln Met Ala Gly Asp Asp Cys
    130                 135                 140

Val Ala Ser Arg Gln Asp Glu Asp
145                 150

<210> SEQ ID NO 30
<211> LENGTH: 332
<212> TYPE: PRT
<213> ORGANISM: Artificial Sequence
<220> FEATURE:
<223> OTHER INFORMATION: HXB2.Pol.94-426 peptide

<400> SEQUENCE: 30

Leu Pro Gly Arg Trp Lys Pro Lys Met Ile Gly Gly Ile Gly Gly Phe
1               5                   10                  15

Ile Lys Val Arg Gln Tyr Asp Gln Ile Leu Ile Glu Ile Cys Gly His
            20                  25                  30

Lys Ala Ile Gly Thr Val Leu Val Gly Pro Thr Pro Val Asn Ile Ile
        35                  40                  45

Gly Arg Asn Leu Leu Thr Gln Ile Gly Cys Thr Leu Asn Phe Pro Ile
    50                  55                  60

Ser Pro Ile Glu Thr Val Pro Val Lys Leu Lys Pro Gly Met Asp Gly
65                  70                  75                  80

Pro Lys Val Lys Gln Trp Pro Leu Thr Glu Glu Lys Ile Lys Ala Leu
                85                  90                  95

Val Glu Ile Cys Thr Glu Met Glu Lys Glu Gly Lys Ile Ser Lys Ile
            100                 105                 110

Gly Pro Glu Asn Pro Tyr Asn Thr Pro Val Phe Ala Ile Lys Lys Lys
        115                 120                 125

Asp Ser Thr Lys Trp Arg Lys Leu Val Asp Phe Arg Glu Leu Asn Lys
    130                 135                 140

Arg Thr Gln Asp Phe Trp Glu Val Gln Leu Gly Ile Pro His Pro Ala
145                 150                 155                 160

Gly Leu Lys Lys Lys Lys Ser Val Thr Val Leu Asp Val Gly Asp Ala
                165                 170                 175
```

```
Tyr Phe Ser Val Pro Leu Asp Glu Asp Phe Arg Lys Tyr Thr Ala Phe
            180                 185                 190

Thr Ile Pro Ser Ile Asn Asn Glu Thr Pro Gly Ile Arg Tyr Gln Tyr
            195                 200                 205

Asn Val Leu Pro Gln Gly Trp Lys Gly Ser Pro Ala Ile Phe Gln Ser
            210                 215                 220

Ser Met Thr Lys Ile Leu Glu Pro Phe Arg Lys Gln Asn Pro Asp Ile
225                 230                 235                 240

Val Ile Tyr Gln Tyr Met Asp Asp Leu Tyr Val Gly Ser Asp Leu Glu
            245                 250                 255

Ile Gly Gln His Arg Thr Lys Ile Glu Glu Leu Arg Gln His Leu Leu
            260                 265                 270

Arg Trp Gly Leu Thr Thr Pro Asp Lys Lys His Gln Lys Glu Pro Pro
            275                 280                 285

Phe Leu Trp Met Gly Tyr Glu Leu His Pro Asp Lys Trp Thr Val Gln
            290                 295                 300

Pro Ile Val Leu Pro Glu Lys Asp Ser Trp Thr Val Asn Asp Ile Gln
305                 310                 315                 320

Lys Leu Val Gly Lys Leu Asn Trp Ala Ser Gln Ile
            325                 330

<210> SEQ ID NO 31
<211> LENGTH: 86
<212> TYPE: PRT
<213> ORGANISM: Artificial Sequence
<220> FEATURE:
<223> OTHER INFORMATION: Mcon.Env.516-601 peptide

<400> SEQUENCE: 31

Gly Phe Leu Gly Ala Ala Gly Ser Thr Met Gly Ala Ala Ser Ile Thr
1               5                   10                  15

Leu Thr Val Gln Ala Arg Gln Leu Leu Ser Gly Ile Val Gln Gln Gln
            20                  25                  30

Ser Asn Leu Leu Arg Ala Ile Glu Ala Gln Gln His Leu Leu Gln Leu
        35                  40                  45

Thr Val Trp Gly Ile Lys Gln Leu Gln Ala Arg Val Leu Ala Val Glu
    50                  55                  60

Arg Tyr Leu Lys Asp Gln Gln Leu Leu Gly Ile Trp Gly Cys Ser Gly
65                  70                  75                  80

Lys Leu Ile Cys Thr Thr
                85

<210> SEQ ID NO 32
<211> LENGTH: 231
<212> TYPE: PRT
<213> ORGANISM: Artificial Sequence
<220> FEATURE:
<223> OTHER INFORMATION: Mcon.Gag.133-363 peptide

<400> SEQUENCE: 32

Pro Ile Val Gln Asn Leu Gln Gly Gln Met Val His Gln Ala Ile Ser
1               5                   10                  15

Pro Arg Thr Leu Asn Ala Trp Val Lys Val Val Glu Glu Lys Ala Phe
            20                  25                  30

Ser Pro Glu Val Ile Pro Met Phe Ser Ala Leu Ser Glu Gly Ala Thr
        35                  40                  45

Pro Gln Asp Leu Asn Thr Met Leu Asn Thr Val Gly Gly His Gln Ala
```

```
                    50                  55                  60
Ala Met Gln Met Leu Lys Asp Thr Ile Asn Glu Glu Ala Ala Glu Trp
 65                  70                  75                  80

Asp Arg Leu His Pro Val His Ala Gly Pro Ile Pro Pro Gly Gln Met
                     85                  90                  95

Arg Glu Pro Arg Gly Ser Asp Ile Ala Gly Thr Thr Ser Thr Leu Gln
                100                 105                 110

Glu Gln Ile Gly Trp Met Thr Ser Asn Pro Pro Ile Pro Val Gly Glu
            115                 120                 125

Ile Tyr Lys Arg Trp Ile Ile Leu Gly Leu Asn Lys Ile Val Arg Met
        130                 135                 140

Tyr Ser Pro Val Ser Ile Leu Asp Ile Arg Gln Gly Pro Lys Glu Pro
145                 150                 155                 160

Phe Arg Asp Tyr Val Asp Arg Phe Phe Lys Thr Leu Arg Ala Glu Gln
                165                 170                 175

Ala Thr Gln Asp Val Lys Asn Trp Met Thr Asp Thr Leu Leu Val Gln
            180                 185                 190

Asn Ala Asn Pro Asp Cys Lys Thr Ile Leu Lys Ala Leu Gly Pro Gly
        195                 200                 205

Ala Thr Leu Glu Glu Met Met Thr Ala Cys Gln Gly Val Gly Gly Pro
    210                 215                 220

Ser His Lys Ala Arg Val Leu
225                 230

<210> SEQ ID NO 33
<211> LENGTH: 69
<212> TYPE: PRT
<213> ORGANISM: Artificial Sequence
<220> FEATURE:
<223> OTHER INFORMATION: Mcon.Gag.391-459 peptide

<400> SEQUENCE: 33

Lys Cys Phe Asn Cys Gly Lys Glu Gly His Ile Ala Arg Asn Cys Arg
  1               5                  10                  15

Ala Pro Arg Lys Lys Gly Cys Trp Lys Cys Gly Lys Glu Gly His Gln
                 20                  25                  30

Met Lys Asp Cys Thr Glu Arg Gln Ala Asn Phe Leu Gly Lys Ile Trp
             35                  40                  45

Pro Ser Asn Lys Gly Arg Pro Gly Asn Phe Leu Gln Ser Arg Pro Glu
         50                  55                  60

Pro Thr Ala Pro Pro
 65

<210> SEQ ID NO 34
<211> LENGTH: 182
<212> TYPE: PRT
<213> ORGANISM: Artificial Sequence
<220> FEATURE:
<223> OTHER INFORMATION: Mcon.Pol.94-275 peptide

<400> SEQUENCE: 34

Leu Pro Gly Lys Trp Lys Pro Lys Met Ile Gly Gly Ile Gly Gly Phe
  1               5                  10                  15

Ile Lys Val Arg Gln Tyr Asp Gln Ile Leu Ile Glu Ile Cys Gly Lys
                 20                  25                  30

Lys Ala Ile Gly Thr Val Leu Val Gly Pro Thr Pro Val Asn Ile Ile
             35                  40                  45
```

Gly Arg Asn Met Leu Thr Gln Ile Gly Cys Thr Leu Asn Phe Pro Ile
 50                  55                  60

Ser Pro Ile Glu Thr Val Pro Val Lys Leu Lys Pro Gly Met Asp Gly
 65                  70                  75                  80

Pro Lys Val Lys Gln Trp Pro Leu Thr Glu Glu Lys Ile Lys Ala Leu
                 85                  90                  95

Thr Glu Ile Cys Thr Glu Met Glu Lys Glu Gly Lys Ile Ser Lys Ile
            100                 105                 110

Gly Pro Glu Asn Pro Tyr Asn Thr Pro Ile Phe Ala Ile Lys Lys Lys
        115                 120                 125

Asp Ser Thr Lys Trp Arg Lys Leu Val Asp Phe Arg Glu Leu Asn Lys
130                 135                 140

Arg Thr Gln Asp Phe Trp Glu Val Gln Leu Gly Ile Pro His Pro Ala
145                 150                 155                 160

Gly Leu Lys Lys Lys Lys Ser Val Thr Val Leu Asp Val Gly Asp Ala
                165                 170                 175

Tyr Phe Ser Val Pro Leu
            180

<210> SEQ ID NO 35
<211> LENGTH: 37
<212> TYPE: PRT
<213> ORGANISM: Artificial Sequence
<220> FEATURE:
<223> OTHER INFORMATION: Mcon.Pol.363-399 peptide

<400> SEQUENCE: 35

His Leu Leu Arg Trp Gly Phe Thr Thr Pro Asp Lys Lys His Gln Lys
  1               5                  10                  15

Glu Pro Pro Phe Leu Trp Met Gly Tyr Glu Leu His Pro Asp Lys Trp
             20                  25                  30

Thr Val Gln Pro Ile
         35

<210> SEQ ID NO 36
<211> LENGTH: 29
<212> TYPE: PRT
<213> ORGANISM: Artificial Sequence
<220> FEATURE:
<223> OTHER INFORMATION: Mcon.Pol.482-510 peptide

<400> SEQUENCE: 36

Ala Glu Ile Gln Lys Gln Gly Gln Asp Gln Trp Thr Tyr Gln Ile Tyr
  1               5                  10                  15

Gln Glu Pro Phe Lys Asn Leu Lys Thr Gly Lys Tyr Ala
             20                  25

<210> SEQ ID NO 37
<211> LENGTH: 58
<212> TYPE: PRT
<213> ORGANISM: Artificial Sequence
<220> FEATURE:
<223> OTHER INFORMATION: Mcon.Pol.741-798 peptide

<400> SEQUENCE: 37

Phe Asn Leu Pro Pro Ile Val Ala Lys Glu Ile Val Ala Ser Cys Asp
  1               5                  10                  15

Lys Cys Gln Leu Lys Gly Glu Ala Met His Gly Gln Val Asp Cys Ser
             20                  25                  30

Pro Gly Ile Trp Gln Leu Asp Cys Thr His Leu Glu Gly Lys Ile Ile

-continued

```
                35                  40                  45

Leu Val Ala Val His Val Ala Ser Gly Tyr
    50                  55

<210> SEQ ID NO 38
<211> LENGTH: 152
<212> TYPE: PRT
<213> ORGANISM: Artificial Sequence
<220> FEATURE:
<223> OTHER INFORMATION: Mcon.Pol.852-1003 peptide

<400> SEQUENCE: 38

Gln Glu Phe Gly Ile Pro Tyr Asn Pro Gln Ser Gln Gly Val Val Glu
1               5                   10                  15

Ser Met Asn Lys Glu Leu Lys Lys Ile Ile Gly Gln Val Arg Asp Gln
                20                  25                  30

Ala Glu His Leu Lys Thr Ala Val Gln Met Ala Val Phe Ile His Asn
            35                  40                  45

Phe Lys Arg Lys Gly Gly Ile Gly Gly Tyr Ser Ala Gly Glu Arg Ile
    50                  55                  60

Ile Asp Ile Ile Ala Thr Asp Ile Gln Thr Lys Glu Leu Gln Lys Gln
65                  70                  75                  80

Ile Thr Lys Ile Gln Asn Phe Arg Val Tyr Tyr Arg Asp Ser Arg Asp
                85                  90                  95

Pro Ile Trp Lys Gly Pro Ala Lys Leu Leu Trp Lys Gly Glu Gly Ala
            100                 105                 110

Val Val Ile Gln Asp Asn Ser Glu Ile Lys Val Val Pro Arg Arg Lys
        115                 120                 125

Ala Lys Ile Ile Arg Asp Tyr Gly Lys Gln Met Ala Gly Asp Asp Cys
    130                 135                 140

Val Ala Gly Arg Gln Asp Glu Asp
145                 150

<210> SEQ ID NO 39
<211> LENGTH: 333
<212> TYPE: PRT
<213> ORGANISM: Artificial Sequence
<220> FEATURE:
<223> OTHER INFORMATION: Mcon.Pol.94-426 peptide

<400> SEQUENCE: 39

Leu Pro Gly Lys Trp Lys Pro Lys Met Ile Gly Gly Ile Gly Gly Phe
1               5                   10                  15

Ile Lys Val Arg Gln Tyr Asp Gln Ile Leu Ile Glu Ile Cys Gly Lys
                20                  25                  30

Lys Ala Ile Gly Thr Val Leu Val Gly Pro Thr Pro Val Asn Ile Ile
            35                  40                  45

Gly Arg Asn Met Leu Thr Gln Ile Gly Cys Thr Leu Asn Phe Pro Ile
    50                  55                  60

Ser Pro Ile Glu Thr Val Pro Val Lys Leu Lys Pro Gly Met Asp Gly
65                  70                  75                  80

Pro Lys Val Lys Gln Trp Pro Leu Thr Glu Glu Lys Ile Lys Ala Leu
                85                  90                  95

Thr Glu Ile Cys Thr Glu Met Glu Lys Glu Gly Lys Ile Ser Lys Ile
            100                 105                 110

Gly Pro Glu Asn Pro Tyr Asn Thr Pro Ile Phe Ala Ile Lys Lys Lys
        115                 120                 125
```

```
Asp Ser Thr Lys Trp Arg Lys Leu Val Asp Phe Arg Glu Leu Asn Lys
    130             135             140
Arg Thr Gln Asp Phe Trp Glu Val Gln Leu Gly Ile Pro His Pro Ala
145             150             155             160
Gly Leu Lys Lys Lys Ser Val Thr Val Leu Asp Val Gly Asp Ala
            165             170             175
Tyr Phe Ser Val Pro Leu Asp Glu Asp Phe Arg Lys Tyr Thr Ala Phe
            180             185             190
Thr Ile Pro Ser Ile Asn Asn Glu Thr Pro Gly Ile Arg Tyr Gln Tyr
        195             200             205
Asn Val Leu Pro Gln Gly Trp Lys Gly Ser Pro Ala Ile Phe Gln Ser
    210             215             220
Ser Met Thr Lys Ile Leu Glu Pro Phe Arg Thr Gln Asn Pro Glu Ile
225             230             235             240
Val Ile Tyr Gln Tyr Met Asp Asp Leu Tyr Val Gly Ser Asp Leu Glu
            245             250             255
Ile Gly Gln His Arg Thr Lys Ile Glu Glu Leu Arg Glu His Leu Leu
            260             265             270
Arg Trp Gly Phe Thr Thr Pro Asp Lys Lys His Gln Lys Glu Pro Pro
            275             280             285
Phe Leu Trp Met Gly Tyr Glu Leu His Pro Asp Lys Trp Thr Val Gln
    290             295             300
Pro Ile Gln Leu Pro Glu Lys Asp Ser Trp Thr Val Asn Asp Ile Gln
305             310             315             320
Lys Leu Val Gly Lys Leu Asn Trp Ala Ser Gln Ile Tyr
            325             330
```

MOSAIC CONSERVED REGION HIV IMMUNOGENIC POLYPEPTIDES

CROSS REFERENCE TO RELATED APPLICATIONS

This is the § 371 U.S. National Stage of International Application No. PCT/US2014/058422, filed Sep. 30, 2014, which was published in English under PCT Article 21(2), which in turn claims the benefit of U.S. Provisional Application No. 61/884,705, filed Sep. 30, 2013, which is incorporated by reference herein in its entirety.

The Sequence_Listing is submitted as an ASCII text file in the form of the file named Sequence_Listing.txt, which was created on Mar. 25, 2016, and is 45,604 bytes, which is incorporated by reference herein.

ACKNOWLEDGMENT OF GOVERNMENT SUPPORT

This invention was made with government support under Contract No. DE-AC52-06NA25396 awarded by the U.S. Department of Energy and grant number AI100645 from the National Institutes of Health. The government has certain rights in the invention.

FIELD

This disclosure relates to immunogenic polypeptides, particularly polypeptides that can elicit an immune response to human immunodeficiency virus (HIV) in a subject.

BACKGROUND

Approximately 35 million people worldwide are estimated to be infected with human immunodeficiency virus (HIV). Although infection rates are declining, in 2012 about 2.3 million people were newly infected and about 1.6 million people died from AIDS-related illnesses. Thus, there remains a need for the development of effective vaccines to treat and inhibit HIV infection worldwide. However, viral diversity in HIV and the occurrence of T cell escape variants provide significant challenges to development of effective HIV vaccines.

SUMMARY

Disclosed herein are mosaic conserved region HIV polypeptides that can elicit an immune response to HIV (such as cytotoxic T cell (CTL), helper T cell, and/or humoral responses). Also disclosed herein are immunogenic polypeptides including one or more of the mosaic conserved region polypeptides. In some examples, two or more of the mosaic conserved region polypeptides are included in a fusion (or chimeric) immunogenic polypeptide. In some embodiments, the disclosed immunogenic polypeptides are included in an immunogenic composition, such as a polyvalent immunogenic composition.

Also disclosed herein are methods for treating or inhibiting HIV in a subject including administering one or more (such as two or more) of the disclosed immunogenic polypeptides or compositions to a subject infected with HIV or at risk of HIV infection. Also disclosed are methods of inducing an immune response to HIV in a subject by administering to the subject at least one (such as two or more) of the immunogenic polypeptides or a nucleic acid encoding at least one of the immunogenic polypeptides disclosed herein.

The foregoing and other features of the disclosure will become more apparent from the following detailed description, which proceeds with reference to the accompanying figures.

BRIEF DESCRIPTION OF THE DRAWINGS

FIGS. 1A and 1B are sets of plots showing population coverage of potential epitopes in Gag, Nef, Pol, and Env (FIG. 1A) in the first generation design or in Gag and Pol (FIG. 1B) in the second generation design. Starting at each position in the alignment, the fraction of 9-mers matched by one of the two candidates in the population are shown in black, and the fraction that are only off by one amino acid are shown in gray. The fraction that matches the two most common forms in that region is shown by the dotted black line. The peptides that carry epitopes that are associated with a good outcome (low viral load) are shown in lightly shaded bars at the bottom of each plot and those associated with a high viral load are shown as dark shaded gray bars (Mothe et al., *J. Transl. Med.* 9:208, 2011). The boxed regions show the regions selected for the conserved region mosaic polypeptide. The bars above the plots show the conserved regions used for a previously described design (Letourneau et al., *PLoS One* 2:e894, 2007).

FIGS. 2A and 2B are sets of plots showing population coverage of potential epitopes in Tat, Rev, Vif, Vpr, and Vpu (FIG. 2A; first generation design) or in Tat, Rev, Vif, Vpr, Vpu, Nef, and Env (FIG. 2B; second generation design), labeled as described in FIGS. 1A and 1B.

FIGS. 3A and 3B are pairs of plots showing the eight regions included (top) and the regions of HIV excluded (bottom) in the first generation design (FIG. 3A) and the second generation design (FIG. 3B), labeled as described in FIGS. 1A and 1B.

FIGS. 4A and 4B are pairs of plots showing the frequency of experimentally defined T-cell responses monitored in the HIV database. The regions in the conserved region mosaic polypeptide first generation design (FIG. 4A) and the second generation design (FIG. 4B) are shaded. The regions each encompass multiple T cell responses that have been detected in natural infections. Top, cytotoxic T cell (CTL) responses; bottom, helper T cell responses.

SEQUENCE LISTING

The nucleic acid and amino acid sequences disclosed herein and in the accompanying sequence listing are shown using standard letter abbreviations for nucleotide bases, and one letter code for amino acids. Only one strand of each nucleic acid sequence is shown, but the complementary strand is understood as included by any reference to the displayed strand.

SEQ ID NOs: 1-18 are exemplary mosaic HIV conserved region polypeptides.

SEQ ID NOs: 19 and 20 are additional exemplary mosaic Pol conserved region polypeptides.

SEQ ID NO: 21 is the amino acid sequence of a tissue plasminogen activator leader peptide.

SEQ ID NOs: 22-30 are the amino acid sequences of HBX2 reference sequence corresponding to the mosaic HIV conserved region peptides.

SEQ ID NOs: 31-39 are the amino acid sequences of consensus sequences of the mosaic HIV conserved region peptides.

DETAILED DESCRIPTION

Disclosed herein are HIV mosaic polypeptides that can elicit an immune response to HIV (such as cytotoxic T cell (CTL), helper T cell, and/or humoral responses). The disclosed mosaic polypeptides include conserved regions from stretches of different natural HIV strains, selected from the full Los Alamos National Laboratory database of HIV sequences (available on the World Wide Web at hiv.lanl.gov) to yield the maximum epitope coverage of the global population of HIV. In particular, the polypeptides span the most conserved regions of the HIV proteome and are mosaic to capture the most common variants. In some embodiments, two or more of the mosaic polypeptides (also referred to as "conserved region polypeptides" or "mosaic conserved region polypeptides") are included in a chimeric or fusion polypeptide.

The disclosed polypeptides can be administered to a subject to elicit an immune response to HIV. In some embodiments, the polypeptides are included in a polyvalent immunogenic composition that includes two or more of the disclosed mosaic conserved region polypeptides. These polyvalent compositions are designed to capture the most common variants of epitope-length fragments. Previous studies indicate that full length mosaic proteins can elicit T cell responses that generate both more responses that cross-recognize natural strains (greater breadth) and responses that recognize more natural variants per response (greater depth) than previous HIV immunogenic compositions (Santra et al., *Nat. Med.* 16:324-328, 2010). The disclosed mosaic polypeptides are focused on the conserved regions, to generate a more effective and focused immune response.

I. Terms

Unless otherwise noted, technical terms are used according to conventional usage. Definitions of common terms in molecular biology can be found in Benjamin Lewin, *Genes VII*, published by Oxford University Press, 1999; Kendrew et al. (eds.), *The Encyclopedia of Molecular Biology*, published by Blackwell Science Ltd., 1994; and Robert A. Meyers (ed.), *Molecular Biology and Biotechnology: a Comprehensive Desk Reference*, published by VCH Publishers, Inc., 1995; and other similar references.

As used herein, the singular forms "a," "an," and "the," refer to both the singular as well as plural, unless the context clearly indicates otherwise. For example, the term "an antigen" includes single or plural antigens and can be considered equivalent to the phrase "at least one antigen." As used herein, the term "comprises" means "includes." Thus, "comprising an antigen" means "including an antigen" without excluding other elements.

It is further to be understood that any and all base sizes or amino acid sizes, and all molecular weight or molecular mass values, given for nucleic acids or polypeptides are approximate, and are provided for descriptive purposes, unless otherwise indicated. Although many methods and materials similar or equivalent to those described herein can be used, particular suitable methods and materials are described below. In case of conflict, the present specification, including explanations of terms, will control. In addition, the materials, methods, and examples are illustrative only and not intended to be limiting.

To facilitate review of the various embodiments of the disclosure, the following explanations of terms are provided:

Adjuvant: A vehicle or composition used to enhance antigenicity. Adjuvants include a suspension of minerals (alum, aluminum hydroxide, or phosphate) on which antigen is adsorbed; or water-in-oil emulsion in which antigen solution is emulsified in mineral oil (Freund incomplete adjuvant), sometimes with the inclusion of killed mycobacteria (Freund's complete adjuvant) to further enhance antigenicity (inhibits degradation of antigen and/or causes influx of macrophages). Immunostimulatory oligonucleotides (such as those including a CpG motif) can also be used as adjuvants (for example see U.S. Pat. No. 6,194,388; U.S. Pat. No. 6,207,646; U.S. Pat. No. 6,214,806; U.S. Pat. No. 6,218,371; U.S. Pat. No. 6,239,116; U.S. Pat. No. 6,339,068; U.S. Pat. No. 6,406,705; and U.S. Pat. No. 6,429,199). Adjuvants include biological molecules (a "biological adjuvant"), such as costimulatory molecules. Exemplary adjuvants include IL-2, RANTES, GM-CSF, TNF-$\alpha$, IFN-$\gamma$, G-CSF, LFA-3, CD72, B7-1, B7-2, OX-40L and 41 BBL. Adjuvants can be used in combination with the disclosed conserved region polypeptides and immunogenic chimeric polypeptides.

Administration: The introduction of a composition into a subject by a chosen route. For example, if the chosen route is intravenous, the composition (such as a disclosed antigen) is administered by introducing the composition intramuscularly into a subject.

Antigen: A compound, composition, or substance that can stimulate the production of antibodies or a T cell response in a subject, including compositions that are injected or absorbed into a subject. An antigen reacts with the products of specific humoral or cellular immunity, including those induced by heterologous antigens, such as the disclosed antigens. "Epitope" or "antigenic determinant" refers to the region of an antigen to which B and/or T cells respond. In one embodiment, T cells respond to the epitope, when the epitope is presented in conjunction with an MHC molecule. Epitopes can be formed both from contiguous amino acids or noncontiguous amino acids juxtaposed by tertiary folding of a protein. Epitopes formed from contiguous amino acids are typically retained on exposure to denaturing solvents whereas epitopes formed by tertiary folding are typically lost on treatment with denaturing solvents. An epitope typically includes at least 3, and more usually, at least 5, about 9, or about 8-10 amino acids in a unique spatial conformation. Methods of determining spatial conformation of epitopes include, for example, x-ray crystallography and nuclear magnetic resonance.

Examples of antigens include, but are not limited to, peptides, lipids, polysaccharides, and nucleic acids containing antigenic determinants, such as those recognized by an immune cell. In some examples, antigens include peptides derived from a pathogen of interest. Exemplary pathogens include bacteria, fungi, viruses and parasites. In specific examples, an antigen is derived from HIV, for example, one or more HIV polypeptides or a fragment thereof, such as at least a portion of an Env, Gag, or Pol protein.

Fusion (or chimeric) polypeptide: A polypeptide including two or more linked peptides to produce a single polypeptide chain, such as a non-naturally occurring polypeptide chain. In some examples, the fusion polypeptide (also referred to herein as a chimeric polypeptide) includes two or more peptides that are directly linked by a peptide bond. In other examples, the fusion polypeptide includes two or more peptides that are indirectly linked (for example by an intervening linker).

HXB2 numbering system: A reference numbering system for HIV protein and nucleic acid sequences (Korber et al., Human Retroviruses and AIDS 1998: A Compilation and Analysis of Nucleic Acid and Amino Acid Sequences. Korber B, Kuiken C L, Foley B, Hahn B, McCutchan F, Mellors J W, and Sodroski J, Eds.; Theoretical Biology and Biophysics Group, Los Alamos National Laboratory, Los Alamos, N. Mex., which is incorporated by reference herein in its entirety). The HXB2 system uses HIV-1 HXB2 strain sequences as a reference for all other HIV strain sequences. The person of ordinary skill in the art is familiar with the HXB2 numbering system. HXB2 is also known as: HXBc2, for HXB clone 2; HXB2R, in the Los Alamos HIV database, with the R for revised, as it was slightly revised relative to the original HXB2 sequence; and HXB2CG in the NCBI GenBank database, for HXB2 complete genome. The numbering used in the conserved region insert polypeptides disclosed herein is relative to the HXB2 numbering scheme.

Host cells: Cells in which a virus or vector can be propagated and its DNA expressed. The cell may be prokaryotic or eukaryotic. The term also includes any progeny of the subject host cell. It is understood that all progeny may not be identical to the parental cell since there may be mutations that occur during replication. However, such progeny are included when the term "host cell" is used.

Immunogenic polypeptide: A protein or a portion thereof that is capable of inducing an immune response in a subject, such as a subject infected or at risk of infection with a pathogen. Administration of an immunogenic polypeptide derived from a pathogen of interest can induce an immune response. Administration of an immunogenic polypeptide can in some examples lead to protective immunity against a pathogen of interest. In some examples, an immunogenic polypeptide is a polypeptide including one or more conserved regions from an HIV proteome, for example, a chimeric or fusion protein including two or more of the disclosed HIV conserved region polypeptides.

Immune response: A response of a cell of the immune system, such as a B cell, T cell, or monocyte, to a stimulus. In one embodiment, the response is specific for a particular antigen (an "antigen-specific response"). In one embodiment, an immune response is a T cell response, such as a CD4+ response or a CD8+ response. In another embodiment, the response is a B cell response, and results in the production of specific antibodies.

Immunogenic composition: A composition comprising an immunogenic polypeptide or a nucleic acid encoding an immunogenic polypeptide that induces a measurable CTL response against virus expressing the immunogenic polypeptide or a portion thereof, induces a measurable helper T cell response, or induces a measurable B cell response (such as production of antibodies) against the immunogenic polypeptide or a portion thereof. In one example, an "immunogenic composition" is composition including one or more conserved region polypeptides from HIV, such as the conserved regions disclosed herein. It further refers to isolated nucleic acids encoding an immunogenic polypeptide, such as a nucleic acid that can be used to express the immunogenic polypeptide (and thus be used to elicit an immune response against the polypeptide or a portion thereof).

For in vitro use, an immunogenic composition may consist of at least one (such as two or more) isolated polypeptide, peptide epitope, or nucleic acid encoding the polypeptide or peptide epitope. For in vivo use, the immunogenic composition will typically include at least one (such as one, two, three, four, five, or more) polypeptide, peptide, or nucleic acid in pharmaceutically acceptable carriers, and/or other agents (such as adjuvant(s)). Any particular peptide, such as a disclosed conserved region polypeptide or a nucleic acid encoding the polypeptide, can be readily tested for its ability to induce a CTL, helper T cell, or B cell response by art-recognized assays. Immunogenic compositions can include adjuvants, which are well known to one of skill in the art.

Inhibiting or treating a disease: Inhibiting the full development of a disease or condition, for example, in a subject who is at risk for a disease such as acquired immune deficiency syndrome (AIDS), AIDS related conditions, HIV infection (such as HIV-1 infection), or combinations thereof. "Treatment" refers to a therapeutic intervention that ameliorates a sign or symptom of a disease or pathological condition (such as AIDS or AIDS-related conditions) after it has begun to develop. The term "ameliorating," with reference to a disease or pathological condition, refers to any observable beneficial effect of the treatment. The beneficial effect can be evidenced, for example, by a delayed onset of clinical symptoms of the disease in a susceptible subject, a reduction in severity of some or all clinical symptoms of the disease, a slower progression of the disease, an improvement in the overall health or well-being of the subject, or by other parameters well known in the art that are specific to the particular disease. A "prophylactic" treatment is a treatment administered to a subject who does not exhibit signs of a disease or exhibits only early signs of a disease for the purpose of decreasing the risk of developing pathology.

Isolated: An "isolated" biological component (such as a protein, for example a disclosed polypeptide or nucleic acid encoding such a polypeptide) has been substantially separated or purified away from other biological components in which the component naturally occurs, such as other chromosomal and extrachromosomal DNA, RNA, and proteins. Proteins, peptides, and nucleic acids that have been "isolated" include proteins purified by standard purification methods. The term also embraces proteins or peptides prepared by recombinant expression in a host cell as well as chemically synthesized proteins, peptides, and nucleic acid molecules. Isolated does not require absolute purity, and can include protein, peptide, or nucleic acid molecules that are at least 50% isolated, such as at least 75%, 80%, 90%, 95%, 98%, 99%, or even 99.9% isolated.

Mosaic polypeptide: A polypeptide assembled from fragments of natural sequences via computational optimization (e.g., Fischer et al., *Nat. Med.* 13:100-106, 2007). Multiple sequences (for example, thousands of sequences) are used as input and the sequences are evolved by recombination in silico. Recombinants are constrained to have natural breakpoints and a mosaic set is designed to maximize coverage of potential T cell epitopes for a viral population.

Operably linked: A first nucleic acid is operably linked with a second nucleic acid when the first nucleic acid is placed in a functional relationship with the second nucleic acid. For instance, a promoter is operably linked to a coding sequence if the promoter affects the transcription or expression of the coding sequence. Generally, operably linked nucleic acids are contiguous and, where necessary to join two protein-coding regions, in the same reading frame. In some examples, the operably linked nucleic acids are heterologous, for example, the first and second nucleic acids are from different organisms, different genes, or different polypeptides and the resulting nucleic acid is not naturally occurring.

Pharmaceutically acceptable carriers: The pharmaceutically acceptable carriers useful in this disclosure are conventional. *Remington: The Science and Practice of Phar-*

*macy*, The University of the Sciences in Philadelphia, Editor, Lippincott, Williams, & Wilkins, Philadelphia, Pa., 21$^{st}$ Edition (2005), describes compositions and formulations suitable for pharmaceutical delivery of the proteins, nucleic acids, and other compositions herein disclosed.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions, powder, pill, tablet, or capsule forms, conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Polypeptide: Any compound composed of amino acids, amino acid analogs, chemically bound together. The term polypeptide as used herein includes oligomers of amino acids, amino acid analogs, or small and large peptides, including proteins. Any chain of amino acids, regardless of length or post-translational modification (such as glycosylation or phosphorylation) is referred to as a polypeptide. The term polypeptide applies to amino acid polymers including naturally occurring amino acid polymers and non-naturally occurring amino acid polymers as well as polymers in which one or more amino acid residue is a non-natural amino acid, for example an artificial chemical mimetic of a corresponding naturally occurring amino acid. As used herein, polypeptide also refers to recombinant amino acid polymers, such as polymers including portions that are obtained from different (typically non-contiguous) portions of a genome (such as an HIV genome) and/or are obtained from different genomes (such as two or more HIV strains). A "residue" refers to an amino acid or amino acid mimetic incorporated in a polypeptide by an amide bond or amide bond mimetic.

Polyvalent immunogenic composition: A composition including two or more separate immunogenic polypeptides (such as a "cocktail" of immunogenic polypeptides) that are capable of eliciting an immune response in a subject, for example an immune response to HIV. In some examples, a polyvalent immunogenic composition includes two or more of the disclosed mosaic conserved region polypeptides (or nucleic acids encoding the polypeptides). In some examples, a polyvalent immunogenic composition includes two mosaic polypeptides that were computationally optimized to be used in combination to provide optimal global coverage of epitope variants. In one specific example, a polyvalent immunogenic composition includes a polypeptide comprising the amino acids sequences of each of SEQ ID NOs: 1-8 or each of SEQ ID NOs: 1, 2, 3, 6, 7, 8, and 17 and a polypeptide comprising the amino acid sequences of each of SEQ ID NOs: 9-16 or each of SEQ ID NOs: 9, 10, 11, 14, 15, 16, and 18.

Purified: The term purified does not require absolute purity; rather, it is intended as a relative term. Thus, for example, a purified protein is one in which the protein is more enriched than the protein is in its natural environment within a cell. Preferably, a preparation is purified such that the protein represents at least 50% of the protein content of the preparation.

Recombinant nucleic acid or polypeptide: A nucleic acid molecule or polypeptide that is not naturally occurring or has a sequence that is made by an artificial combination of two otherwise separated segments of nucleotide or amino acid sequence. This artificial combination is accomplished by chemical synthesis or, more commonly, by the artificial manipulation of isolated segments of nucleic acids, e.g., by genetic engineering techniques such as those described in Sambrook et al. (ed.), *Molecular Cloning: A Laboratory Manual*, 2$^{nd}$ ed., vol. 1-3, Cold Spring Harbor Laboratory Press, Cold Spring Harbor, N.Y., 1989. The term "recombinant" includes nucleic acids or polypeptides that have been altered solely by addition, substitution, or deletion of a portion of a natural nucleic acid molecule or peptide.

Sequence identity/similarity: Sequence identity between two or more nucleic acid sequences or between two or more amino acid sequences can be measured in terms of percentage identity; the higher the percentage, the more identical the sequences are. Homologs or orthologs of nucleic acid or amino acid sequences possess a relatively high degree of sequence identity/similarity when aligned using standard methods.

Methods of alignment of sequences for comparison are well known in the art. Various programs and alignment algorithms are described in: Smith & Waterman, *Adv. Appl. Math.* 2:482, 1981; Needleman & Wunsch, *J. Mol. Biol.* 48:443, 1970; Pearson & Lipman, *Proc. Natl. Acad. Sci. USA* 85:2444, 1988; Higgins & Sharp, *Gene*, 73:237-44, 1988; Higgins & Sharp, *CABIOS* 5:151-3, 1989; Corpet et al., *Nuc. Acids Res.* 16:10881-90, 1988; Huang et al. *Computer Appls. in the Biosciences* 8, 155-65, 1992; and Pearson et al., *Meth. Mol. Bio.* 24:307-31, 1994. Altschul et al., *J. Mol. Biol.* 215:403-10, 1990, presents a detailed consideration of sequence alignment methods and homology calculations. The NCBI Basic Local Alignment Search Tool (BLAST) (Altschul et al., *J. Mol. Biol.* 215:403-10, 1990) is available from several sources, including the National Center for Biological Information (NCBI, National Library of Medicine, Building 38A, Room 8N805, Bethesda, Md. 20894) and on the Internet, for use in connection with the sequence analysis programs blastp, blastn, blastx, tblastn, and tblastx. Blastn is used to compare nucleic acid sequences, while blastp is used to compare amino acid sequences. Additional information can be found at the NCBI web site.

In some examples, sequence similarity is assessed by the conservation of epitope-length fragments. The use of this measure of similarity was developed at Los Alamos National Laboratory, and tools are available on the World Wide Web at hiv.lanl.gov.

Subject: Living multi-cellular vertebrate organisms, a category that includes both human and non-human mammals (including non-human primates).

Therapeutically effective amount or Effective amount: The amount of agent, such as nucleic acid, polypeptide, or other therapeutic agent, that is sufficient to prevent, treat (including prophylaxis), reduce, and/or ameliorate the symptoms and/or underlying causes of any of a disorder or disease, for example to prevent, inhibit, and/or treat HIV. In some embodiments, an "effective amount" is sufficient to reduce or eliminate a symptom of a disease, such as AIDS. For instance, this can be the amount necessary to inhibit viral replication or to measurably alter outward symptoms of the viral infection, such as increase T cell counts in the case of an HIV infection. In general, this amount will be sufficient to measurably inhibit virus (for example, HIV) replication or infectivity. An "anti-viral agent" or "anti-viral drug" is an agent that specifically inhibits a virus from replicating or infecting cells. Similarly, an "anti-retroviral agent" is an agent that specifically inhibits a retrovirus from replicating or infecting cells.

Cell: A white blood cell critical to the immune response. T cells include, but are not limited to, $CD4^+$ T cells and $CD8^+$ T cells. A $CD4^+$ T lymphocyte is an immune cell that carries a marker on its surface known as "cluster of differentiation 4" (CD4). These cells, also known as helper T cells, help orchestrate the immune response, including antibody responses as well as killer T cell responses. $CD8^+$ T cells carry the "cluster of differentiation 8" (CD8) marker. In one embodiment, a CD8 T cell is a cytotoxic T lymphocyte (CTL). In another embodiment, a CD8 cell is a suppressor T cell.

Transformed: A transformed cell is a cell into which has been introduced a nucleic acid molecule by molecular biology techniques. As used herein, the term transformation encompasses all techniques by which a nucleic acid molecule might be introduced into such a cell, including transfection with viral vectors, transformation with plasmid vectors, and introduction of DNA by electroporation, lipofection, and particle gun acceleration.

Vaccine: A pharmaceutical composition that elicits a prophylactic or therapeutic immune response in a subject. In some cases, the immune response is a protective immune response and can block subsequent infection, in other cases it can limit the pathological impact of an infection by containing the infection. Typically, a vaccine elicits an antigen-specific immune response to an antigen of a pathogen, for example a viral pathogen, or to a cellular constituent correlated with a pathological condition. A vaccine may include a polynucleotide (such as a nucleic acid encoding a disclosed antigen), a peptide or polypeptide (such as a disclosed antigen), a virus, a cell, or one or more cellular constituents.

Vector: A nucleic acid molecule that can be introduced into a host cell, thereby producing a transformed host cell. Recombinant DNA vectors are vectors having recombinant DNA. A vector can include nucleic acid sequences that permit it to replicate in a host cell, such as an origin of replication. A vector can also include one or more selectable marker genes and other genetic elements known in the art. Viral vectors are recombinant DNA vectors having at least some nucleic acid sequences derived from one or more viruses.

Virus: A virus consists essentially of a core of nucleic acid surrounded by a protein coat, and has the ability to replicate only inside a living cell. "Viral replication" is the production of additional virus by the occurrence of at least one viral life cycle. A virus may subvert the host cell's normal functions, causing the cell to behave in a manner determined by the virus. For example, a viral infection may result in a cell producing a cytokine, or responding to a cytokine, when the uninfected cell does not normally do so. In some examples, a virus is a pathogen.

"Retroviruses" are RNA viruses wherein the viral genome is RNA. When a host cell is infected with a retrovirus, the genomic RNA is reverse transcribed into a DNA intermediate which is integrated very efficiently into the chromosomal DNA of infected cells. The integrated DNA intermediate is referred to as a provirus. The term "lentivirus" is used in its conventional sense to describe a genus of viruses containing reverse transcriptase. The lentiviruses include the "immunodeficiency viruses" which include human immunodeficiency virus (HIV) type 1 and type 2 (HIV-1 and HIV-2), simian immunodeficiency virus (SIV), and feline immunodeficiency virus (FIV).

HIV-1 is a retrovirus that causes immunosuppression in humans (HIV disease), and leads to a disease complex known as the acquired immunodeficiency syndrome (AIDS). "HIV disease" refers to a well-recognized constellation of signs and symptoms (including the development of opportunistic infections) in persons who are infected by an HIV virus, as determined by antibody or western blot studies or detection of HIV nucleic acids. Laboratory findings associated with this disease include a progressive decline in T cells.

II. Description of Several Embodiments

Disclosed herein are mosaic conserved region polypeptides from HIV proteins. The mosaic conserved region polypeptides include regions of HIV proteins (such as Gag, Pol, and/or Env proteins) that are the most highly conserved between different HIV strains. Mosaic polypeptides are assembled from fragments of natural sequences via a computational optimization method (e.g., U.S. Pat. App. Publ. No. 2012/0231028, incorporated herein by reference in its entirety). Mosaic polypeptides resemble polypeptides from natural proteins, but do not exist in nature. Thousands of sequences are use used as input, and the sequences are evolved by recombination in silico. Recombinants are constrained to have natural breakpoints, and a mosaic set will maximize the coverage of potential T-cell epitopes (peptides of nine amino acids) present as variants for a viral population (such as HIV). Combinations of mosaics are selected to give the optimal coverage of potential epitopes found in natural sequences for a given number of mosaics. The mosaic conserved region polypeptides disclosed herein are described in greater detail in Section IIA and Examples 1 and 2.

The mosaic conserved region polypeptides and nucleic acids encoding the polypeptides disclosed herein are capable of eliciting an immune response to HIV in a subject. In some embodiments, two or more conserved region polypeptides (or nucleic acids encoding the polypeptides) are assembled into a linked chain (for example, a chimeric or fusion polypeptide or a nucleic acid encoding a chimeric or fusion polypeptide). The term "immunogenic polypeptide" is used herein to refer to individual conserved region polypeptides as well as chimeric or fusion polypeptides disclosed herein.

A. Immunogenic Polypeptides

Exemplary amino acid sequences of HIV protein mosaic conserved region polypeptides designed as described in Examples 1 and 2, include SEQ ID NOs: 1-18 disclosed herein. In some examples, the mosaic conserved region polypeptides include, consist essentially of, or consist of an amino acid sequence at least 95% identical to the amino acid sequence set forth as one of SEQ ID NOs: 1-18, such as at least 95% identical, at least 96% identical, at least 97% identical, at least 98% identical, at least 99% identical, or even 100% identical to the sequence set forth as one of SEQ ID NOs: 1-18. The amino acid numbering provided for each fragment is with respect to the HXB2 numbering scheme. The designation "2.1" or "2.2" identifies the two independent mosaic sequences, which typically capture the most common variants of epitope-length fragments (Table 1). The amino acid sequences of the corresponding HXB2 sequence as a comparator for analysis are provided herein as SEQ ID NOs: 22-30 and consensus versions (Mcon) for comparisons of 2.1 versus 2.2 sequences are provided herein as SEQ ID NOs: 31-39.

TABLE 1

Amino acid numbering for mosaic conserved region peptides

| SEQ ID NO: | HXB2 numbering |
|---|---|
| 1 | Mos.Env.2.1.516-601 |
| 2 | Mos.Gag.2.1.133-363 |
| 3 | Mos.Gag.2.1.391-459 |
| 4 | Mos.Pol.2.1.94-275 |
| 5 | Mos.Pol.2.1.363-399 |
| 6 | Mos.Pol.2.1.482-510 |
| 7 | Mos.Pol.2.1.741-798 |
| 8 | Mos.Pol.2.1.852-1003 |
| 9 | Mos.Env.2.2.516-601 |
| 10 | Mos.Gag.2.2.133-363 |
| 11 | Mos.Gag.2.2.391-459 |
| 12 | Mos.Pol.2.2.94-275 |
| 13 | Mos.Pol.2.2.363-399 |
| 14 | Mos.Pol.2.2.482-510 |
| 15 | Mos.Pol.2.2.741-798 |
| 16 | Mos.Pol.2.2.852-1003 |
| 17 | Mos.Pol.2.1.94-426 |
| 18 | Mos.Pol.2.2.94-426 |

In some embodiments, an immunogenic polypeptide comprises one or more (such as 1, 2, 3, 4, 5, 6, 7, 8, 9, 10, 11, 12, 13, 14, 15, 16, 17, or 18) of the disclosed mosaic conserved region polypeptides (such as one or more of SEQ ID NOs: 1-18). In some examples, two or more of the mosaic conserved region polypeptides are linked to form a single immunogenic polypeptide (for example, a chimeric or fusion polypeptide).

In particular examples, the two or more linked mosaic conserved region polypeptides include two or more (such as 2, 3, 4, 5, 6, 7, 8, or all) of SEQ ID NOs: 1-8, or sequences having at least 95% identity to any one of SEQ ID NOs: 1-8. In one example, an immunogenic polypeptide includes amino acid sequences including, consisting essentially of, or consisting of all of SEQ ID NOs: 1-8. In another particular example, the two or more linked conserved region polypeptides include two or more (such as 2, 3, 4, 5, 6, or all) of SEQ ID NOs: 1, 2, 3, 6, 7, 8, and 17, or sequences having at least 95% identity to any one of SEQ ID NOs: 1, 2, 3, 6, 7, 8, and 17. In one example an immunogenic polypeptide includes amino acid sequences including, consisting essentially of, or consisting of all of SEQ ID NOs: 1, 2, 3, 6, 7, 8, and 17. In yet another example, the two or more linked conserved region polypeptides include two or more (such as 2, 3, 4, 5, or all) of SEQ ID NOs: 2, 3, 5, 6, 7, 8, and 17, such as an immunogenic polypeptide including amino acids sequences including, consisting essentially of, or consisting of all of SEQ ID NOs: 2, 3, 5, 6, 7, 8, and 17.

In other particular examples, the two or more linked conserved region polypeptides include two or more (such as 2, 3, 4, 5, 6, 7, or all) of SEQ ID NOs: 9-16 or sequences having at least 95% identity to any one of SEQ ID NOs: 9-16. In one example, an immunogenic polypeptide includes all of SEQ ID NOs: 1-9. In another particular example, the two or more linked conserved regions include two or more (such as 2, 3, 4, 5, 6, or all) of SEQ ID NOs: 9, 10, 11, 14, 15, 16, and 18. In one example, an immunogenic polypeptide includes amino acid sequences including, consisting essentially of, or consisting of all of SEQ ID NOs: 9, 10, 11, 14, 15, 16, and 18. In yet another example, the two or more linked conserved region polypeptides include two or more (such as 2, 3, 4, 5, or all) of SEQ ID NOs: 10, 11, 14, 15, 16, and 18, such as an immunogenic polypeptide including amino acids sequences including, consisting essentially of, or consisting of all of SEQ ID NOs: 10, 11, 14, 15, 16, and 18.

In some examples, a leader or signal peptide is linked to the immunogenic polypeptide, for example to increase expression and/or immunogenicity of the polypeptide. In one example, the leader peptide is a tissue plasminogen activator (tPA) leader peptide, for example, a peptide having the amino acid sequence MDAMKRGLCCVLLLC-GAVFVSAR (SEQ ID NO: 21). One of skill in the art can identify other suitable leader peptides that can be used to optimize expression of the disclosed polypeptides.

In some embodiments, the disclosed immunogenic polypeptides include one or more peptide linkers, for example to attach two or more conserved region polypeptides in a single polypeptide chain. Linker peptides are typically a short amino acid sequence providing a flexible linker that permits attachment of polypeptides, such as a conserved region polypeptide, without disruption of the structure, aggregation (e.g., multimerization), or activity of the polypeptide component. Typically, a linear linking peptide consists of between two and 25 amino acids. Usually, the linear linking peptide is between two and 15 amino acids in length, although in certain circumstances it can be only one, such as a single glycine residue. In one example, the linker polypeptide is two to three amino acids in length, such as a serine and an arginine, or two serine residues and an arginine residue, or two arginine residues and a serine residue, two glycines and a serine, two serines and a glycine or any combination thereof. One of ordinary skill in the art can identify additional suitable linkers (e.g., Chaudhary et al., *Nature* 339:394-397, 1989).

In some embodiments, the conserved region polypeptides are included in a chimeric or fusion polypeptide (immunogenic polypeptide) in a selected order. In some examples, the order of the conserved region polypeptides is selected to minimize the immune responses directed towards non-naturally occurring peptide junctions in the fusion polypeptides. Exemplary orders of the mosaic conserved region polypeptides in a fusion polypeptide are shown in Table 2. However, these are only examples, and the immunogenic polypeptide can include the amino acid sequences of any of SEQ ID NOs: 1-8 and 17 or SEQ ID NOs: 9-16 and 18 in any order.

TABLE 2

Exemplary mosaic conserved region fusion polypeptides

| Construct Name | Sequence Order (N-terminus to C-terminus) |
|---|---|
| tHIVconsv1 | SEQ ID NO: 2, SEQ ID NO: 3, SEQ ID NO: 17, SEQ ID NO: 6, SEQ ID NO: 7, SEQ ID NO: 8 |
| tHIVconsv2 | SEQ ID NO: 11, SEQ ID NO: 14, SEQ ID NO: 16, SEQ ID NO: 10, SEQ ID NO: 18, SEQ ID NO: 15 |
| tHIVconsv3 | SEQ ID NO: 17, SEQ ID NO: 8, SEQ ID NO: 3, SEQ ID NO: 7, SEQ ID NO: 2, SEQ ID NO: 6 |
| tHIVconsv4 | SEQ ID NO: 14, SEQ ID NO: 10, SEQ ID NO: 15, SEQ ID NO: 11, SEQ ID NO: 16, SEQ ID NO: 18 |
| tHIVconsv5 | SEQ ID NO: 7, SEQ ID NO: 17, SEQ ID NO: 2, SEQ ID NO: 8, SEQ ID NO: 6, SEQ ID NO: 3 |
| tHIVconsv6 | SEQ ID NO: 16, SEQ ID NO: 15, SEQ ID NO: 14, SEQ ID NO: 18, SEQ ID NO: 11, SEQ ID NO: 10 |
| tHIVconsv7 | SEQ ID NO: 1, SEQ ID NO: 2, SEQ ID NO: 3, SEQ ID NO: 17, SEQ ID NO: 6, SEQ ID NO: 7, SEQ ID NO: 8 |
| tHIVconsv8 | SEQ ID NO: 9, SEQ ID NO: 10, SEQ ID NO: 11, SEQ ID NO: 18, SEQ ID NO: 14, SEQ ID NO: 15, SEQ ID NO: 16 |
| tHIVconsv9 | SEQ ID NO: 8, SEQ ID NO: 7, SEQ ID NO: 6, SEQ ID NO: 17, SEQ ID NO: 3, SEQ ID NO: 2, SEQ ID NO: 1 |
| tHIVconsv10 | SEQ ID NO: 16, SEQ ID NO: 15, SEQ ID NO: 14, SEQ ID NO: 18, SEQ ID NO: 11, SEQ ID NO: 10, SEQ ID NO: 9 |

TABLE 2-continued

Exemplary mosaic conserved region fusion polypeptides

| Construct Name | Sequence Order (N-terminus to C-terminus) |
|---|---|
| tHIVconsv11 | SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8 |
| tHIVconsv12 | SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16 |
| tHIVconsv13 | SEQ ID NO: 8, SEQ ID NO: 7, SEQ ID NO: 6, SEQ ID NO: 5, SEQ ID NO: 4, SEQ ID NO: 3, SEQ ID NO: 2, SEQ ID NO: 1 |
| tHIVconsv14 | SEQ ID NO: 16, SEQ ID NO: 15, SEQ ID NO: 14, SEQ ID NO: 13, SEQ ID NO: 12, SEQ ID NO: 11SEQ ID NO: 10, SEQ ID NO: 9 |

In some embodiments, the immunogenic polypeptides are provided as sets of immunogenic polypeptides. In one example a set of immunogenic polypeptides includes tHIVconsv1 and tHIVconsv2. In another example, a set of immunogenic polypeptides includes tHIVconsv3 and tHIVconsv4. In yet another example, a set of immunogenic polypeptides includes tHIVconsv5 and tHIVconsv6. In particular embodiments, the sets of immunogenic polypeptides are administered to a subject (discussed in more detail in Section III, below). In some examples, a set of immunogenic polypeptides is included in an immunogenic composition.

The immunogenic polypeptides disclosed herein can be chemically synthesized by standard methods, or can be produced recombinantly, for example by expression of the polypeptide from a nucleic acid molecule that encodes the polypeptide. An exemplary process for polypeptide production is described in Lu et al., *FEBS Lett.* 429:31-35, 1998. They can also be isolated by methods including preparative chromatography and immunological separations.

B. Nucleic Acids

Nucleic acids encoding the disclosed conserved region polypeptides (e.g. SEQ ID NOs: 1-18) and the disclosed chimeric or fusion polypeptides including two or more of the conserved region polypeptides are also disclosed herein. Unless otherwise specified, a "nucleic acid encoding a polypeptide" includes all nucleotide sequences that are degenerate versions of each other and encode the same amino acid sequence. For example, a polynucleotide encoding a disclosed immunogenic polypeptide includes a nucleic acid sequence that is degenerate as a result of the genetic code. There are 20 natural amino acids, most of which are specified by more than one codon. Therefore, all degenerate nucleotide sequences are included as long as the amino acid sequence of the polypeptide encoded by the nucleotide sequence is unchanged. In some embodiments, the polypeptide sequences are back-translated to codon optimized DNA using standard methods.

The nucleic acids encoding a conserved region polypeptide or an immunogenic polypeptide (such as a chimeric polypeptide including two or more of the disclosed conserved region polypeptides) include a recombinant DNA which is incorporated into a vector, such as an autonomously replicating plasmid or virus, or into the genomic DNA of a prokaryote or eukaryote, or which exists as a separate molecule (such as a cDNA) independent of other sequences. Methods for the manipulation and insertion of the nucleic acids of this disclosure into vectors are well known in the art (see for example, Sambrook et al., *Molecular Cloning, a Laboratory Manual*, 2d edition, Cold Spring Harbor Press, Cold Spring Harbor, N.Y., 1989, and Ausubel et al., *Current Protocols in Molecular Biology*, Greene Publishing Associates and John Wiley & Sons, New York, N.Y., 1994). DNA sequences encoding the polypeptide can be expressed in vitro or in vivo by DNA transfer into a suitable host cell. The cell may be prokaryotic or eukaryotic. Methods of stable transfer, meaning that the foreign DNA is continuously maintained in the host, are known in the art.

Polynucleotide sequences encoding the disclosed polypeptides can be operatively linked to expression control sequences. An expression control sequence operatively linked to a coding sequence is ligated such that expression of the coding sequence is achieved under conditions compatible with the expression control sequences. The expression control sequences include, but are not limited to, appropriate promoters, enhancers, transcription terminators, a start codon (i.e., ATG) in front of a protein-encoding gene, splicing signal for introns, maintenance of the correct reading frame of that gene to permit proper translation of mRNA, and stop codons.

Hosts can include microbial, yeast, insect and mammalian organisms. Methods of expressing DNA sequences having eukaryotic or viral sequences in prokaryotes are well known in the art. Non-limiting examples of suitable host cells include bacteria, archaea, insect, fungi (for example, yeast), plant, and animal cells (for example, mammalian cells, such as human cells). Exemplary cells of use include *Escherichia coli, Bacillus subtilis, Saccharomyces cerevisiae, Salmonella typhimurium*, SF9 cells, C129 cells, *Neurospora*, and immortalized mammalian myeloid and lymphoid cell lines. Techniques for the propagation of mammalian cells in culture are well-known (see, Jakoby and Pastan (eds), 1979, Cell Culture, Methods in Enzymology, volume 58, Academic Press, Inc., Harcourt Brace Jovanovich, N.Y.). Examples of commonly used mammalian host cell lines are VERO and HeLa cells, CHO cells, HEK 293 cells, and WI38, BHK, and COS cell lines, although other cell lines may be used, such as cells designed to provide higher expression, desirable glycosylation patterns, or other features.

A number of viral vectors have been constructed, that can be used to express the disclosed polypeptides, including polyoma, e.g., SV40 (Madzak et al., 1992, *J. Gen. Virol.*, 73:1533-1536); adenovirus (Berkner, 1992, *Cur. Top. Microbiol. Immunol.*, 158:39-6; Berliner et al., 1988, *Bio Techniques*, 6:616-629; Gorziglia et al., 1992, *J. Virol.*, 66:4407-4412; Quantin et al., 1992, *Proc. Natl. Acad. Sci. USA*, 89:2581-2584; Rosenfeld et al., 1992, *Cell*, 68:143-155; Wilkinson et al., 1992, *Nucl. Acids Res.*, 20:2233-2239; Stratford-Perricaudet et al., 1990, *Hum. Gene Ther.*, 1:241-256); non-replicating adenoviruses of chimpanzee origin (ChAdv; Tatsis et al., *Gene Ther.* 13:421-429, 2006); vaccinia virus (Mackett et al., 1992, *Biotechnology*, 24:495-499); modified vaccinia Ankara (MVA) virus (Kremer et al., *Methods Mol. Biol.* 890:59-92, 2012); adeno-associated virus (Muzyczka, 1992, *Curr. Top. Microbiol. Immunol.*, 158:91-123; On et al., 1990, *Gene*, 89:279-282); herpes viruses, including HSV and EBV (Margolskee, 1992, *Curr. Top. Microbiol. Immunol.*, 158:67-90; Johnson et al., 1992, *J. Virol.*, 66:2952-2965; Fink et al., 1992, *Hum. Gene Ther.* 3:11-19; Breakfield et al., 1987, *Mol. Neurobiol.*, 1:337-371; Fresse et al., 1990, *Biochem. Pharmacol.*, 40:2189-2199); Sindbis viruses (Herweijer et al., 1995, *Human Gene Therapy* 6:1161-1167; U.S. Pat. Nos. 5,091,309 and 5,2217, 879); alphaviruses (Schlesinger, 1993, *Trends Biotechnol.* 11:18-22; Frolov et al., 1996, *Proc. Natl. Acad. Sci.* USA 93:11371-11377); and retroviruses of avian (Brandyopadhyay et al., 1984, *Mol. Cell Biol.*, 4:749-754; Petropouplos et al., 1992, *J. Virol.*, 66:3391-3397), murine (Miller, 1992, *Curr. Top. Microbiol. Immunol.*, 158:1-24; Miller et al., 1985, *Mol. Cell Biol.*, 5:431-437; Sorge et al., 1984, *Mol. Cell Biol.*, 4:1730-1737; Mann et al., 1985, *J. Virol.*, 54:401-407), and human origin (Page et al., 1990, *J. Virol.*, 64:5370-5276; Buchschalcher et al., 1992, *J. Virol.*, 66:2731-2739). Baculovirus (*Autographa californica* multinuclear polyhedrosis virus; AcMNPV) vectors are also known in the art, and may be obtained from commercial sources (such as PharMingen, San Diego, Calif.; Protein Sciences Corp., Meriden, Conn.; Stratagene, La Jolla, Calif.).

III. Therapeutic Methods and Pharmaceutical Compositions

The immunogenic polypeptides disclosed herein (such as at least one of SEQ ID NOs: 1-18 or fusion proteins including two or more of SEQ ID NOs: 1-18), or nucleic acids encoding the disclosed immunogenic polypeptides, can be administered to a subject to elicit an immune response in the subject, such as an immune response to HIV. In some embodiments, a composition including one or more of the disclosed polypeptides (or one or more nucleic acids encoding the disclosed polypeptides) is administered to a subject with HIV infection (for example, as a therapeutic immunization) or at risk of HIV infection (for example as a protective immunization), for example to treat or inhibit HIV infection. In other embodiments, the composition is administered to a subject as part of an immunization regimen. The composition is administered in an amount sufficient to elicit an immune response to HIV in the subject. In some examples, administration of the composition inhibits (or in some instances even prevents) infection with HIV and/or reduces the signs and symptoms of HIV in an infected subject.

In particular embodiments, two or more of the disclosed polypeptides or nucleic acids encoding the polypeptides are administered to the subject. In some examples, the methods include administering to the subject at least two polypeptides, each including the same conserved region(s) of the HIV proteome, but from different strains of HIV and thus differing in amino acid sequence by one or more amino acids (for example, a polyvalent immunogenic composition). In one particular example, the methods include administering to the subject a first immunogenic polypeptide including amino acid sequences comprising, consisting essentially of, or consisting of SEQ ID NOs: 1-8 and a second immunogenic polypeptide including amino acid sequences comprising or consisting of SEQ ID NOs: 9-16. In other examples, the methods include administering to the subject a first immunogenic polypeptide including amino acid sequences comprising, consisting essentially of, or consisting of SEQ ID NOs: 1, 2, 3, 6, 7, 8, and 17 and a second immunogenic polypeptide including amino acid sequences comprising, consisting essentially of, or consisting of SEQ ID NOs: 9, 10, 11, 14, 15, 16, and 18. In one example, the methods include administering to the subject a first immunogenic polypeptide comprising tHIVconsv1 and a second immunogenic polypeptide comprising tHIVconsv2. In another example, the methods include administering to the subject a first immunogenic polypeptide comprising tHIVconsv3 and a second immunogenic polypeptide comprising tHIVconsv4. In a still further example, the methods include administering to the subject a first immunogenic polypeptide comprising tHIVconsv5 and a second immunogenic polypeptide comprising tHIVconsv6.

In some examples, the two or more immunogenic polypeptides are administered simultaneously (for example, as a mixture), substantially simultaneously (for example, within a few minutes of one another, such as within less than 5 minutes of one another), or sequentially (for example, within 5 minutes, 10 minutes, 15 minutes, 30 minutes, 1 hour, 2 hours, 4 hours, 12 hours, 24, hours, or more of one another).

One or more of the disclosed polypeptides or nucleic acids encoding the polypeptides (including vectors including the nucleic acid) can be administered by any means known to one of skill in the art (see Banga, "Parenteral Controlled Delivery of Therapeutic Peptides and Proteins," in *Therapeutic Peptides and Proteins*, Technomic Publishing Co., Inc., Lancaster, Pa., 1995) either locally or systemically, such as by intramuscular, subcutaneous, or intravenous injection, but even oral, nasal, or anal administration is contemplated. In one embodiment, administration is by subcutaneous or intramuscular injection. To extend the time during which the disclosed polypeptides are available to stimulate a response, the polypeptide or nucleic acid encoding the polypeptide can be provided as an implant, an oily injection, or as a particulate system. The particulate system can be a microparticle, a microcapsule, a microsphere, a nanocapsule, or similar particle. (See, e.g., Banga, supra.) A particulate carrier based on a synthetic polymer has been shown to act as an adjuvant to enhance the immune response, in addition to providing a controlled release. Aluminum salts can also be used as adjuvants to produce an immune response.

Optionally, one or more cytokines, such as interleukin (IL)-2, IL-6, IL-12, IL-15, RANTES, granulocyte macrophage colony stimulating factor (GM-CSF), tumor necrosis factor (TNF)-α, interferon (IFN)-α or IFN-γ, one or more growth factors, such as GM-CSF or G-CSF, one or more costimulatory molecules, such as ICAM-1, LFA-3, CD72, B7-1, B7-2, or other B7 related molecules; one or more molecules such as OX-40L or 41 BBL, or combinations of these molecules, can be used as biological adjuvants (see, for example, Salgaller et al., 1998, *J. Surg. Oncol.* 68(2): 122-38; Lotze et al., 2000, *Cancer J Sci. Am.* 6(Suppl 1):561-6; Cao et al., 1998, *Stem Cells* 16(Suppl 1):251-60; Kuiper et al., 2000, *Adv. Exp. Med. Biol.* 465:381-90) with the disclosed immunogenic polypeptides. These molecules can be administered systemically (or locally) to the host. In several examples, IL-2, RANTES, GM-CSF, TNF-α, IFN-γ, G-CSF, LFA-3, CD72, B7-1, B7-2, B7-1 B.7-2, OX-40L, 41 BBL and ICAM-1 are administered.

Pharmaceutical compositions including the disclosed mosaic conserved region polypeptides, chimeric polypeptides, and/or nucleic acids encoding the polypeptides are also disclosed herein. The pharmaceutical composition can include one or more of pharmaceutically acceptable carriers, adjuvants (such as those described above), a stabilizing detergent (such as polysorbate 80 (TWEEN® 80), TWEEN® 40, TWEEN® 20, TWEEN® 60, ZWITTERGENT® 3-12, TEEPOL® HB7, and SPAN® 85 detergents, for example, in an amount of approximately 0.05 to 0.5%, such as at about 0.2%), a micelle-forming agent (such as PLURONIC® L62LF, L101, and L64 block copolymer, polyethylene glycol 1000, and TETRONIC® 1501, 150R1, 701, 901, 1301, and 130R1 block copolymer, for example, between 0.5 and 10%, or in an amount between 1.25 and 5%), and an oil (squalene, squalane, eicosane, tetratetracontane, glycerol, and peanut oil or other vegetable oils, for example, in an amount between 1 and 10%, or between 2.5 and 5%). In one embodiment, the pharmaceutical composition includes a mixture of stabilizing detergents, micelle-forming agent, and oil available under the name PROVAX® (IDEC Pharmaceuticals, San Diego, Calif.).

In some embodiments, a pharmaceutical composition includes a nucleic acid encoding a disclosed polypeptide. A therapeutically effective amount of the nucleic acid can be administered to a subject in order to generate an immune response. In various embodiments, the nucleic acid encoding a biological adjuvant (such as those described above) can be cloned into the same vector as the nucleic acid encoding a disclosed polypeptide, or the nucleic acids can be cloned into one or more separate vectors for co-administration. In addition, nonspecific immunomodulating factors such as Bacillus Calmette-Guerin (BCG) and levamisole can be co-administered.

One approach to administration of nucleic acids is direct immunization with plasmid DNA, such as with a mammalian expression plasmid. As described above, the nucleotide sequence encoding the disclosed immunogenic polypeptide(s) can be placed under the control of a promoter to increase expression of the molecule. Immunization by nucleic acid constructs is well known in the art and taught, for example, in U.S. Pat. No. 5,643,578 (which describes methods of immunizing vertebrates by introducing DNA encoding a desired antigen to elicit a cell-mediated or a humoral response), and U.S. Pat. No. 5,593,972 and U.S. Pat. No. 5,817,637 (which describe operably linking a nucleic acid sequence encoding an antigen to regulatory sequences enabling expression). U.S. Pat. No. 5,880,103 describes several methods of delivery of nucleic acids encoding immunogenic peptides or other antigens to an organism. The methods include liposomal delivery of the nucleic acids (or of the synthetic peptides themselves), and immune-stimulating constructs, or ISCOMs, negatively charged cage-like structures of 30-40 nm in size formed spontaneously on mixing cholesterol and Quil A™ (saponin).

In another approach to using nucleic acids for immunization, a disclosed immunogenic polypeptide can also be expressed by attenuated viral hosts or vectors or bacterial vectors. Recombinant vaccinia virus, adeno-associated virus (AAV), herpes virus, retrovirus, cytomegalovirus or other viral vectors (such as those described above) can be used to express the peptide or protein. For example, vaccinia vectors and methods useful in immunization protocols are described in U.S. Pat. No. 4,722,848. BCG (Bacillus Calmette Guerin) provides another vector for expression of the peptides (see Stover, *Nature* 351:456-460, 1991).

In one embodiment, a nucleic acid encoding a disclosed immunogenic polypeptide is introduced directly into cells. For example, the nucleic acid can be loaded onto gold microspheres by standard methods and introduced into the skin by a device such as HELIOS™ Gene Gun (Bio-Rad). The nucleic acids can be "naked," consisting of plasmids under control of a strong promoter. Typically, the DNA is injected into muscle, although it can also be injected directly into other sites The amount of the disclosed immunogenic polypeptide, or nucleic acid molecule encoding the immunogenic polypeptide can vary depending upon the specific polypeptide(s), the route and protocol of administration, and the target population. In some embodiments, each dose includes about 1 μg to 1 mg of protein, such as from about 1 μg to about 500 μg, for example, from about 1 μg to about 100 μg, or about 1 μg to about 50 μg, such as about 1 μg, about 2 μg, about 5 μg, about 10 μg, about 15 μg, about 20 μg, about 25 μg, about 30 μg, about 40 μg, about 50 μg, about 75 μg, about 100 μg, about 200 μg, about 300 μg, about 400 μg, or about 500 μg. An optimal amount for a particular composition can be ascertained by standard studies involving observation of antibody titers and other responses in subjects (such as CTL or helper T cell responses).

The disclosed conserved region polypeptides or chimeric polypeptides and/or nucleic acids encoding these polypeptides can be used in a multistep immunization regime. In some examples, the regime includes administering to a subject a therapeutically effective amount of a first immunogenic polypeptide (or mixture of immunogenic polypeptides) and boosting the immunogenic response with a second immunogenic polypeptide (or mixture of immunogenic polypeptides) after an appropriate period of time. This method of eliciting such an immune reaction is referred to as a "prime-boost" immunization regimen. Different dosages can be used in a series of sequential inoculations. Thus, a practitioner may administer a relatively large dose in a primary inoculation (prime) and then boost with relatively smaller doses.

In some examples, the immunogenic polypeptide or mixture thereof administered in both the prime and boost inoculations are the same immunogenic polypeptide or mixture thereof. In other examples, the immunogenic polypeptide or mixture thereof administered in the boost is different from that administered in the prime inoculation. Without being bound by theory, it is believed that changing the peptide order in the immunogenic polypeptides for vaccine prime-boosts and for the polyvalent delivery of the immunogenic polypeptides will minimize immune responses directed towards non-naturally occurring peptide junctions in the fusion polypeptides.

For example, the immunogenic composition administered as the prime could include at least two immunogenic polypeptides disclosed herein (such as an immunogenic polypeptide including the sequences of SEQ ID NOs: 1-8, SEQ ID NOs: 1, 2, 3, 6, 7, 8, and 17, or SEQ ID NOs: 2, 3, 6, 7, 8, an 17; and an immunogenic polypeptide including the sequences of SEQ ID NOs: 9-16, SEQ ID NOs: 9, 10, 11, 14, 15, 16, and 18, or SEQ ID NOs: 10, 11, 14, 15, 16, and 18) and the boost could include two different immunogenic polypeptides disclosed herein (such as an immunogenic polypeptide including the sequences of SEQ ID NOs: 1-8, SEQ ID NOs: 1, 2, 3, 6, 7, 8, and 17, or SEQ ID NOs: 2, 3, 6, 7, 8, an 17, in a different order than in the immunogenic polypeptide used in the prime; and an immunogenic polypeptide including the sequences of SEQ ID NOs: 9-16, SEQ ID NOs: 9, 10, 11, 14, 15, 16, and 18, or SEQ ID NOs: 10, 11, 14, 15, 16, and 18, in a different order than in the immunogenic polypeptide used in the prime). In other examples, the prime could include an immunogenic polypeptide including the sequences of SEQ ID NOs: 1-8 and an immunogenic polypeptide including the sequences of SEQ ID NOs: 9-16 and the boost could include an immunogenic polypeptide including the sequences of SEQ ID NOs: 1, 2, 3, 6, 7, 8, and 17 and an immunogenic polypeptide including SEQ ID NOs: 9, 10, 11, 14, 15, 16, and 18, or vice versa. In one example of a prime-boost regimen, the polyvalent combination of tHIVconsv1 and tHIVconsv2 are administered as an initial prime, and serial boosts are administered as tHIVconsv3 and tHIVconsv4, and in some examples, followed tHIVconsv5 and tHIVconsv6. One of skill in the art will understand that these combinations are only examples, and additional combinations of immunogenic polypeptides and different orders of the polypeptides in the fusion polypeptides can also be used.

The prime can be administered as a single dose or multiple doses, for example two doses, three doses, four doses, five doses, six doses or more can be administered to a subject over days, weeks or months. The boost can be administered as a single dose or multiple doses, for example two to six doses, or more can be administered to a subject over a day, a week or months. Multiple boosts can also be given, such one to five, or more. Different dosages can be used in a series of sequential inoculations. For example a relatively large dose in a primary inoculation and then a boost with relatively smaller doses. An immune response against one or more of the conserved region polypeptides can be generated by one or more inoculations of a subject with an immunogenic composition disclosed herein.

The present disclosure is illustrated by the following non-limiting Examples.

EXAMPLES

Example 1

First Generation Conserved Region Mosaic Design

This example describes the design and selection of inserts for a first generation of mosaic conserved region polypeptides.

HIV-1 M group alignments that contain one sequence per person (thousands of sequences are available for each protein in this set, sampled from all over the globe) were obtained from the Los Alamos database (available on the World Wide Web at hiv.lanl.gov). An optimized two mosaic design was made for each HIV protein. The coverage of every 9-mer in each protein alignment by the mosaic vaccine combination was plotted. A total length of 800-900 amino acids for the polypeptide was selected based on the capacity of currently used genetic vaccine vectors. An 80% population coverage cut-off by the two mosaic design was selected to define the most conserved regions that fill the 800-900 amino acid space constraint (FIGS. 1A and 2A). The 80% coverage allows an 8/9 mismatch between the selected insert and the potential epitope. The frequency of global variants of each the potential epitopes (9-mer coverage) that either perfectly matched one of the two mosaics, or was off by one amino acid when compared to the two mosaics was calculated.

To determine the precise break points of each conserved region shown in FIG. 1A, the frequency of every amino acid in the database protein alignments was calculated, and using this information the precise transition points between conserved and variable regions was defined (depicted in the potential epitope coverage figures; FIGS. 1A and 2A). Previous work has described epitopes that had advantageous responses, in terms of being associated with lower viral loads in natural infection, and epitopes that were disadvantageous and associated with higher viral loads (Mothe et al., *J. Transl. Med.* 9:208, 2011). Although the peptides that are associated with viral control are significantly more conserved than those associated with high viremia, these good responses are not always focused in the most conserved stretches of the proteins. Another interpretation of this data is that responses to some proteins are good (e.g., Gag) and others are not good (e.g., Env), and it is the protein, more than the level of conservation, that is driving the good versus bad responses. In light of this, the design spanned regions where the coverage dropped below 80% for a very short stretch if, by including these stretches, more of the favorable response regions could be encompassed. The peptides associated with favorable responses are depicted as shaded boxes in FIGS. 1A, 2A, and 3A, and those associated with negative responses are depicted in light gray. In addition, each of the conserved regions was selected to encompass epitopes that are seen in natural infection (FIG. 4A), to ensure that regions that are immunologically suppressed were not selected.

The design strategy originally included the requirement that each conserved region be at least 30 amino acids long for inclusion. However, as this cutoff was arbitrarily selected, and one exception was made for a 29 amino acid fragment in Pol that is highly conserved and contains a favorable epitope.

It has previously been observed that immune responses to junctional domains (places where two conserved fragments come together creating potential epitopes that do not naturally occur) can be elicited. To minimize the impact of such regions, the design spanned short regions (for example, one or a few positions) that introduce variability, in order to generate somewhat longer fragments and reduce the total number of fragments for inclusion in the polypeptide.

The total length of the selected fragments was 844 amino acids, which is about 30% of the viral proteome. The selected regions include one Env region (SEQ ID NOs: 1 and 9), which contains the most conserved stretch of Env in gp41 (for example, for providing T cell help), two regions in Gag (SEQ ID NOs: 2, 3, 10, and 11) including the whole of p24, which is very intensely recognized in natural infection, and five regions in Pol (SEQ ID NOs: 4-8 and 12-16) which are less intensely recognized in natural infection but are highly conserved. The selected Env region is near the beginning of gp41, spanning the Avery peptide, fusion peptide, and leucine/isoleucine zipper-like sequence. The first Gag region includes almost the entirety of p24. The second Gag region is in p15 and includes some variation, but spans a "good" epitope. The first Pol region selected has intermittent regions where coverage drops for the two mosaics, but the regions are short, so they are not expected to disrupt the very conserved stretches more than would junctional domains. The selected Pol region also spans some of the epitopes that have been previously identified to be associated with a good outcome (Mothe et al., *J. Transl. Med.* 9:208, 2011). The second Pol region is short, but is highly conserved and also spans epitopes associated with good outcome (Id.).

Example 2

Second Generation Conserved Region Mosaic Design

This example describes the design and selection of the inserts for a second generation of mosaic conserved region polypeptides.

The design and selection of the second generation conserved region mosaic polypeptides was as described in Example 1. In this second generation, a single region (SEQ ID NOs: 17 and 18) that spans the Pol regions 1 and 2 of the first design (SEQ ID NOs: 4, 5, 12, and 13) was selected (FIGS. 1B, 2B, 3B, and 4B). This region fully spans the region between the start of Pol region 1 of the first generation design and extends slightly beyond the end of Pol region 2 of the second generation design and replaces these two polypeptides (SEQ ID NOs: 4, 5, 12, and 13). This includes a greater expanse of quite conserved regions and spans additional two peptides (KNPEIVIYQYMDDLYV (SEQ ID NO: 19) and VIYQYMDDLYVGSDL (SEQ ID NO: 20)) that have previously been shown to be quite reactive (Letourneau et al., *PLoS One* 2:e894, 2007). The first additional peptide (SEQ ID NO: 19) encompasses a somewhat variable region and both are embodied in a peptide that was a CTL target previously associated with higher viral load (Mothe et al., *J. Transl. Med.* 9:208, 2011). However, the inclusion of the additional conserved region indicates that the expanded Poll/2 region can be used in the immunogenic composition. Inclusion of the longer conserved region brings the total length of the chimeric polypeptide over 900 amino acids. In order to reduce the length of the chimeric polypeptide to less than 900 amino acids, the original Env mosaic polypeptide (SEQ ID NOs: 1 and 9) was not included in the final selection of polypeptides for inclusion in the design. The remaining mosaic conserved region polypeptides from the first generation design were retained in the second generation design.

Example 3

Immunization of Animals

This example describes exemplary procedures for immunization of animals with the disclosed immunogenic polypeptides. Although particular methods are provided, one of ordinary skill in the art will appreciate that additional methods or variations of the described methods can also be utilized.

In some examples, nucleic acid molecules encoding the disclosed immunogenic polypeptides are cloned into a plasmid or a viral vector (such as an adenoviral vector or a modified Ankara vaccinia virus vector). Study animals (for example, mice or monkeys) are administered plasmid or viral vector nucleic acid intramuscularly. Varying amounts of the nucleic acid can be administered, for example to test for an optimally effective amount.

In other examples nucleic acid molecules encoding the disclosed immunogenic polypeptides are cloned into an expression vector and expressed in a host cell. The polypeptides are purified using standard methods. Study animals (for example, mice or monkeys) are administered the polypeptides intramuscularly or subcutaneously. Varying doses are administered to determine optimal amounts for eliciting an immune response.

Immune responses elicited by the administered immunogenic polypeptides (or nucleic acids encoding the polypeptides) are assessed. For example, cellular immune responses are assessed using cytokine assays and/or interferon-γ ELISPOT assays. Humoral immune responses are assessed by direct ELISA utilizing one or more HIV proteins (such as Env). Neutralization assays (for example, a luciferase based pseudovirus neutralization assay) are also used to assess humoral immune responses.

Example 4

Treatment of HIV in a Subject

This example describes exemplary methods for treating or inhibiting an HIV infection in a subject, such as a human subject, by administration of one or more of the immunogenic polypeptides or one or more nucleic acids encoding the immunogenic polypeptides disclosed herein. Although particular methods, dosages and modes of administrations are provided, one skilled in the art will appreciate that variations can be made without substantially affecting the treatment.

Briefly, the method includes screening subjects to determine if they have HIV, such as HIV-1 or HIV-2. Subjects having HIV are selected for further treatment. In one example, subjects are selected who have increased levels of HIV antibodies in their blood, as detected with an enzyme-linked immunosorbent assay, Western blot, immunofluorescence assay or nucleic acid testing, including viral RNA or proviral DNA amplification methods. In one example, half of the subjects follow the established protocol for treatment of HIV (such as a highly active antiretroviral therapy). The other half follow the established protocol for treatment of HIV (such as treatment with highly active antiretroviral compounds) in combination with administration of the agents including a therapeutically effective amount of a disclosed immunogenic polypeptide that induces an immune response to HIV. However, pre-screening is not required prior to administration of the therapeutic compositions disclosed herein.

In particular examples, the subject is treated prior to diagnosis of AIDS with the administration of a therapeutically effective amount of one or more of the disclosed immunogenic polypeptides. In some examples, the subject is treated with an established protocol for treatment of AIDS (such as a highly active antiretroviral therapy) prior to treatment with the administration of a therapeutic agent that includes one or more of the disclosed immunogenic polypeptides. However, such pre-treatment is not always required and can be determined by a skilled clinician.

Following selection, an effective amount of one or more (such as 2, 3, 4, 5, 6, 7, or more) immunogenic polypeptides disclosed herein, or one or more (such as 2, 3, 4, 5, 6, 7, or more) nucleic acids encoding disclosed immunogenic polypeptides is administered to the subject (such as an adult human or a newborn infant either at risk for contracting HIV or known to be infected with HIV). Additional agents, such as anti-viral agents, can also be administered to the subject simultaneously or prior to or following administration of the disclosed agents. Administration can be achieved by any method known in the art, such as oral administration, inhalation, intravenous, intramuscular, intraperitoneal or subcutaneous.

The amount of the immunogenic composition administered to prevent, reduce, inhibit, and/or treat HIV or a condition associated with it depends on the subject being treated, the severity of the disorder and the manner of administration of the immunogenic composition. Ideally, an effective amount of the immunogenic composition is an amount sufficient to prevent, reduce, and/or inhibit, and/or treat the condition (for example, HIV) in a subject without causing a substantial cytotoxic effect in the subject. An effective amount can be readily determined by one skilled in the art, for example using routine trials establishing dose response curves. In addition, particular exemplary dosages are provided above. The compositions can be administered in a single dose delivery, via continuous delivery over an extended time period, in a repeated administration protocol (for example, by a daily, weekly or monthly repeated administration protocol). In one example, a therapeutically effective amount of a disclosed polypeptide that induces an immune response to HIV is administered intravenously or intramuscularly to a human. As such, these compositions may be formulated with an inert diluent or with a pharmaceutically acceptable carrier. Immunogenic compositions can be administered long term (for example over a period of months or years).

Following the administration of one or more therapies, subjects having HIV (for example, HIV-1 or HIV-2) can be monitored for reductions in HIV levels, increases in a subject's CD4+ T cell count, or reductions in one or more clinical symptoms associated with HIV infection. In particular examples, subjects are analyzed one or more times, starting 7 days following treatment. Subjects can be monitored using any method known in the art. For example, biological samples from the subject, including blood, can be obtained and alterations in HIV or CD4+ T cell levels evaluated.

In particular examples, if subjects are stable or have a minor, mixed or partial response to treatment, they can be re-treated after re-evaluation with the same or a different schedule and/or preparation of agents that they previously received for the desired amount of time, including the duration of a subject's lifetime. A partial response is a reduction, such as at least a 10%, at least 20%, at least 30%, at least 40%, at least 50% or at least 70% reduction of HIV viral load, HIV replication or combination thereof. A partial response may also be an increase in CD4+ T cell count such as at least 350 T cells per microliter.

Example 5

Treatment of Subjects

This example describes exemplary methods that can be used to treat a subject that has or is at risk of having an infection from HIV that can be treated by eliciting an immune response, such as a neutralizing antibody response to HIV. Although particular methods, dosages and modes of administrations are provided, one skilled in the art will appreciate that variations can be made without substantially affecting the treatment.

In particular examples, the method includes screening a subject having, thought to have or at risk of having a HIV infection. Subjects of an unknown infection status can be examined to determine if they have an infection, for example using serological tests, physical examination, enzyme-linked immunosorbent assay (ELISA), radiological screening or other diagnostic technique known to those of skill in the art. In some examples, subjects are screened to identify a HIV infection, with a serological test, or with a nucleic acid probe specific for a HIV. Subjects found to (or known to) have a HIV infection can be administered one or more disclosed immunogenic polypeptides. Subjects may also be selected who are at risk of developing HIV for example, subjects exposed to HIV.

Subjects selected for treatment can be administered an effective amount of the disclosed immunogenic polypeptides or nucleic acids encoding the disclosed immunogenic polypeptides. The particular dose can be determined by a skilled clinician. The polypeptides (or nucleic acids) can be administered in one or several doses, for example continuously, daily, weekly, or monthly. When administered sequentially the time separating the administration of the doses of the immunogenic polypeptides can be seconds, minutes, hours, days, or even weeks.

Subjects are periodically tested for presence of HIV or HIV antibodies in their blood, as detected with an enzyme-linked immunosorbent assay, Western blot, immunofluorescence assay or nucleic acid testing, including viral RNA or proviral DNA amplification methods.

In view of the many possible embodiments to which the principles of the disclosure may be applied, it should be recognized that the illustrated embodiments are only examples and should not be taken as limiting the scope of the invention. Rather, the scope of the invention is defined by the following claims. We therefore claim as our invention all that comes within the scope and spirit of these claims.

We claim:

1. An isolated immunogenic fusion polypeptide consisting of two or more of the amino acid sequences of SEQ ID NOs: 1-18, or amino acid sequences having at least 95% identity to the amino acid sequence of any one of SEQ ID NOs: 1-18.

2. The isolated immunogenic fusion polypeptide of claim 1, wherein the two or more amino acid sequences consist of:
   each of the amino acid sequences of SEQ ID NOs: 2, 3, 6, 7, 8, and 17;
   amino acid sequences having at least 95% identity to each of SEQ ID NOs: 2, 3, 6, 7, 8, and 17;
   each of SEQ ID NOs: 10, 11, 14, 15, 16, and 18;
   amino acid sequences having at least 95% identity to each of SEQ ID NOs: 10, 11, 14, 15, 16, and 18;
   two or more of SEQ ID NOs: 1-8 and 17;
   two or more amino acid sequences having at least 95% identity to SEQ ID NOs: 1-8 and 17;
   each of the amino acid sequences of SEQ ID NOs: 1-8;
   amino acid sequences having at least 95% identity to each of SEQ ID NOs: 1-8;
   each of SEQ ID NOs: 1, 2, 3, 6, 7, 8, and 17;
   amino acid sequences having at least 95% identity to each of SEQ ID NOs: 1, 2, 3, 6, 7, 8, and 17;
   two or more of SEQ ID NOs: 9-16 and 18;
   two or more amino acid sequences having at least 95% identity to SEQ ID NOs: 9-16 and 18;
   each of SEQ ID NOs: 9-16;
   amino acid sequences having at least 95% identity to each of SEQ ID NOs: 9-16;
   each of SEQ ID NOs: 9, 10, 11, 14, 15, 16, and 18; or
   amino acid sequences having at least 95% identity to each of SEQ ID NOs: 9, 10, 11, 14, 15, 16, and 18.

3. A pharmaceutical composition comprising:
   the isolated immunogenic fusion polypeptide of claim 1; and
   a pharmaceutically acceptable carrier.

4. The pharmaceutical composition of claim 3, further comprising one or more of an adjuvant, a detergent, a micelle-forming agent, and an oil.

5. The isolated immunogenic fusion polypeptide of claim 2, wherein the polypeptide consists of:
   the amino acid sequence of each of SEQ ID NO: 2, SEQ ID NO: 3, SEQ ID NO: 17, SEQ ID NO: 6, SEQ ID NO: 7, and SEQ ID NO: 8, in N-terminus to C-terminus order;
   the amino acid sequence of each of SEQ ID NO: 17, SEQ ID NO: 8, SEQ ID NO: 3, SEQ ID NO: 7, SEQ ID NO: 2, and SEQ ID NO: 6, in N-terminus to C-terminus order;
   the amino acid sequence of each of SEQ ID NO: 7, SEQ ID NO: 17, SEQ ID NO: 2, SEQ ID NO: 8, SEQ ID NO: 6, and SEQ ID NO: 3, in N-terminus to C-terminus order;
   the amino acid sequence of each of SEQ ID NO: 11, SEQ ID NO: 14, SEQ ID NO: 16, SEQ ID NO: 10, SEQ ID NO: 18, and SEQ ID NO: 15, in N-terminus to C-terminus order;
   the amino acid sequence of each of SEQ ID NO: 14, SEQ ID NO: 10, SEQ ID NO: 15, SEQ ID NO: 11, SEQ ID NO: 16, and SEQ ID NO: 18, in N-terminus to C-terminus order;
   the amino acid sequence of each of SEQ ID NO: 16, SEQ ID NO: 15, SEQ ID NO: 14, SEQ ID NO: 18, SEQ ID NO: 11, and SEQ ID NO: 10, in N-terminus to C-terminus order;

the amino acid sequence of each of SEQ ID NO: 1, SEQ ID NO: 2, SEQ ID NO: 3, SEQ ID NO: 4, SEQ ID NO: 5, SEQ ID NO: 6, SEQ ID NO: 7, and SEQ ID NO: 8, in N-terminus to C-terminus order;

the amino acid sequence of each of SEQ ID NO: 8, SEQ ID NO: 7, SEQ ID NO: 6, SEQ ID NO: 5, SEQ ID NO: 4, SEQ ID NO: 3, SEQ ID NO: 2, and SEQ ID NO: 1, in N-terminus to C-terminus order;

the amino acid sequence of each of SEQ ID NO: 9, SEQ ID NO: 10, SEQ ID NO: 11, SEQ ID NO: 12, SEQ ID NO: 13, SEQ ID NO: 14, SEQ ID NO: 15, and SEQ ID NO: 16, in N-terminus to C-terminus order;

the amino acid sequence of each of SEQ ID NO: 16, SEQ ID NO: 15, SEQ ID NO: 14, SEQ ID NO: 13, SEQ ID NO: 12, SEQ ID NO: 11, SEQ ID NO: 10, and SEQ ID NO: 9, in N-terminus to C-terminus order;

the amino acid sequence of each of SEQ ID NO: 1, SEQ ID NO: 2, SEQ ID NO: 3, SEQ ID NO: 17, SEQ ID NO: 6, SEQ ID NO: 7, and SEQ ID NO: 8, in N-terminus to C-terminus order;

the amino acid sequence of each of SEQ ID NO: 8, SEQ ID NO: 7, SEQ ID NO: 6, SEQ ID NO: 17, SEQ ID NO: 3, SEQ ID NO: 2, and SEQ ID NO: 1, in N-terminus to C-terminus order;

the amino acid sequence of each of SEQ ID NO: 9, SEQ ID NO: 10, SEQ ID NO: 11, SEQ ID NO: 18, SEQ ID NO: 14, SEQ ID NO: 15, and SEQ ID NO: 16, in N-terminus to C-terminus order; or the amino acid sequence of each of SEQ ID NO: 16, SEQ ID NO: 15, SEQ ID NO: 14, SEQ ID NO: 18, SEQ ID NO: 11, SEQ ID NO: 10, and SEQ ID NO: 9, in N-terminus to C-terminus order.

6. An isolated immunogenic fusion polypeptide consisting of two or more of the amino acid sequences of SEQ ID NOs: 1-18, or amino acid sequences having at least 95% identity to the amino acid sequence of any one of SEQ ID NOs: 1-18, wherein each of the two or more amino acid sequences are separated by a peptide linker.

7. The isolated immunogenic fusion polypeptide of claim 6, wherein the two or more amino acid sequences consist of:
each of the amino acid sequences of SEQ ID NOs: 2, 3, 6, 7, 8, and 17;
amino acid sequences having at least 95% identity to each of SEQ ID NOs: 2, 3, 6, 7, 8, and 17;
each of SEQ ID NOs: 10, 11, 14, 15, 16, and 18;
amino acid sequences having at least 95% identity to each of SEQ ID NOs: 10, 11, 14, 15, 16, and 18;
two or more of SEQ ID NOs: 1-8 and 17;
two or more amino acid sequences having at least 95% identity to SEQ ID NOs: 1-8 and 17;
each of the amino acid sequences of SEQ ID NOs: 1-8;
amino acid sequences having at least 95% identity to each of SEQ ID NOs: 1-8;
each of SEQ ID NOs: 1, 2, 3, 6, 7, 8, and 17;
amino acid sequences having at least 95% identity to each of SEQ ID NOs: 1, 2, 3, 6, 7, 8, and 17;
two or more of SEQ ID NOs: 9-16 and 18;
two or more amino acid sequences having at least 95% identity to SEQ ID NOs: 9-16 and 18;
each of SEQ ID NOs: 9-16;
amino acid sequences having at least 95% identity to each of SEQ ID NOs: 9-16;
each of SEQ ID NOs: 9, 10, 11, 14, 15, 16, and 18; or
amino acid sequences having at least 95% identity to each of SEQ ID NOs: 9, 10, 11, 14, 15, 16, and 18,
and wherein each of the two or more amino acid sequences are separated by a peptide linker.

8. The isolated immunogenic fusion polypeptide of claim 7, wherein the polypeptide consists of:
the amino acid sequence of each of SEQ ID NO: 2, SEQ ID NO: 3, SEQ ID NO: 17, SEQ ID NO: 6, SEQ ID NO: 7, and SEQ ID NO: 8, in N-terminus to C-terminus order;

the amino acid sequence of each of SEQ ID NO: 17, SEQ ID NO: 8, SEQ ID NO: 3, SEQ ID NO: 7, SEQ ID NO: 2, and SEQ ID NO: 6, in N-terminus to C-terminus order;

the amino acid sequence of each of SEQ ID NO: 7, SEQ ID NO: 17, SEQ ID NO: 2, SEQ ID NO: 8, SEQ ID NO: 6, and SEQ ID NO: 3, in N-terminus to C-terminus order;

the amino acid sequence of each of SEQ ID NO: 11, SEQ ID NO: 14, SEQ ID NO: 16, SEQ ID NO: 10, SEQ ID NO: 18, and SEQ ID NO: 15, in N-terminus to C-terminus order;

the amino acid sequence of each of SEQ ID NO: 14, SEQ ID NO: 10, SEQ ID NO: 15, SEQ ID NO: 11, SEQ ID NO: 16, and SEQ ID NO: 18, in N-terminus to C-terminus order;

the amino acid sequence of each of SEQ ID NO: 16, SEQ ID NO: 15, SEQ ID NO: 14, SEQ ID NO: 18, SEQ ID NO: 11, and SEQ ID NO: 10, in N-terminus to C-terminus order;

the amino acid sequence of each of SEQ ID NO: 1, SEQ ID NO: 2, SEQ ID NO: 3, SEQ ID NO: 4, SEQ ID NO: 5, SEQ ID NO: 6, SEQ ID NO: 7, and SEQ ID NO: 8, in N-terminus to C-terminus order;

the amino acid sequence of each of SEQ ID NO: 8, SEQ ID NO: 7, SEQ ID NO: 6, SEQ ID NO: 5, SEQ ID NO: 4, SEQ ID NO: 3, SEQ ID NO: 2, and SEQ ID NO: 1, in N-terminus to C-terminus order;

the amino acid sequence of each of SEQ ID NO: 9, SEQ ID NO: 10, SEQ ID NO: 11, SEQ ID NO: 12, SEQ ID NO: 13, SEQ ID NO: 14, SEQ ID NO: 15, and SEQ ID NO: 16, in N-terminus to C-terminus order;

the amino acid sequence of each of SEQ ID NO: 16, SEQ ID NO: 15, SEQ ID NO: 14, SEQ ID NO: 13, SEQ ID NO: 12, SEQ ID NO: 11, SEQ ID NO: 10, and SEQ ID NO: 9, in N-terminus to C-terminus order;

the amino acid sequence of each of SEQ ID NO: 1, SEQ ID NO: 2, SEQ ID NO: 3, SEQ ID NO: 17, SEQ ID NO: 6, SEQ ID NO: 7, and SEQ ID NO: 8, in N-terminus to C-terminus order;

the amino acid sequence of each of SEQ ID NO: 8, SEQ ID NO: 7, SEQ ID NO: 6, SEQ ID NO: 17, SEQ ID NO: 3, SEQ ID NO: 2, and SEQ ID NO: 1, in N-terminus to C-terminus order;

the amino acid sequence of each of SEQ ID NO: 9, SEQ ID NO: 10, SEQ ID NO: 11, SEQ ID NO: 18, SEQ ID NO: 14, SEQ ID NO: 15, and SEQ ID NO: 16, in N-terminus to C-terminus order; or the amino acid sequence of each of SEQ ID NO: 16, SEQ ID NO: 15, SEQ ID NO: 14, SEQ ID NO: 18, SEQ ID NO: 11, SEQ ID NO: 10, and SEQ ID NO: 9, in N-terminus to C-terminus order, and wherein each of the amino acid sequences are separated by a peptide linker.

9. A pharmaceutical composition comprising:
the isolated immunogenic fusion polypeptide of claim 6; and
a pharmaceutically acceptable carrier.

10. The pharmaceutical composition of claim 9, further comprising one or more of an adjuvant, a detergent, a micelle-forming agent, and an oil.

11. A method for eliciting an immune response to human immunodeficiency virus (HIV) in a subject, comprising administering to the subject an effective amount of one or more of the isolated immunogenic fusion polypeptides of claim 1, thereby eliciting an immune response to HIV in the subject.

12. The method of claim 11, wherein the one or more isolated immunogenic polypeptides comprise two or more of:
   the isolated immunogenic fusion polypeptide consisting of each of SEQ ID NOs: 1-8;
   the isolated immunogenic fusion polypeptide consisting of each of SEQ ID NOs: 1, 2, 3, 6, 7, 8, and 17;
   the isolated immunogenic fusion polypeptide consisting of each of SEQ ID NOs: 2, 3, 6, 7, 8, and 17;
   the isolated immunogenic fusion polypeptide consisting of each of SEQ ID NOs: 9-16;
   the isolated immunogenic fusion polypeptide consisting of each of SEQ ID NOs: 9, 10, 11, 14, 15, 16, and 18; and
   the isolated immunogenic fusion polypeptide consisting of each of SEQ ID NOs: 10, 11, 14, 15, 16, and 18.

13. The method of claim 12, wherein the two or more isolated immunogenic fusion polypeptides are a polypeptide consisting of SEQ ID NOs: 1-8 and a polypeptide consisting of SEQ ID NOs: 9-16.

14. The method of claim 12, wherein the two or more isolated immunogenic fusion polypeptides are a polypeptide consisting of SEQ ID NOs: 1, 2, 3, 6, 7, 8, and 17, and a polypeptide consisting of SEQ ID NOs: 9, 10, 11, 14, 15, 16, and 18.

15. The method of claim 12, wherein the two or more isolated immunogenic fusion polypeptides are a polypeptide consisting of SEQ ID NOs: 2, 3, 6, 7, 8, and 17, and a polypeptide consisting of SEQ ID NOs: 10, 11, 14, 15, 16, and 18.

16. The method of claim 12, wherein the two or more immunogenic fusion polypeptides are administered to the subject simultaneously, substantially simultaneously, or sequentially.

17. The method of claim 11, further comprising administering to the subject a therapeutically effective amount of an anti-viral agent.

18. A method for eliciting an immune response to human immunodeficiency virus (HIV) in a subject, comprising administering to the subject an effective amount of the pharmaceutical composition of claim 3, thereby eliciting an immune response to HIV in the subject.

19. A method for eliciting an immune response to human immunodeficiency virus (HIV) in a subject, comprising administering to the subject an effective amount of one or more of the isolated immunogenic fusion polypeptides of claim 6, thereby eliciting an immune response to HIV in the subject.

20. A method for eliciting an immune response to human immunodeficiency virus (HIV) in a subject, comprising administering to the subject an effective amount of the pharmaceutical composition of claim 9, thereby eliciting an immune response to HIV in the subject.

\* \* \* \* \*